United States Patent
Chen et al.

(10) Patent No.: US 11,512,073 B2
(45) Date of Patent: Nov. 29, 2022

(54) BENZIMIDAZOLE DERIVATIVES, PHARMACEUTICAL COMPOSITION COMPRISING THE SAME, AND USE THEREOF

(71) Applicant: Chongqing University of Arts and Sciences, Chongqing (CN)

(72) Inventors: Zhongzhu Chen, Chongqing (CN); Zhigang Xu, Chongqing (CN); Dianyong Tang, Chongqing (CN)

(73) Assignee: CHONGQING UNIVERSITY OF ARTS AND SCIENCES, Chongqing (CN)

( * ) Notice: Subject to any disclaimer, the term of this patent is extended or adjusted under 35 U.S.C. 154(b) by 0 days.

(21) Appl. No.: 17/346,161

(22) Filed: Jun. 11, 2021

(65) Prior Publication Data

US 2021/0387970 A1 Dec. 16, 2021

Related U.S. Application Data

(60) Provisional application No. 63/038,268, filed on Jun. 12, 2020.

(51) Int. Cl.
| | |
|---|---|
| *C07D 403/04* | (2006.01) |
| *C07D 405/14* | (2006.01) |
| *C07D 409/14* | (2006.01) |
| *A61P 35/00* | (2006.01) |

(52) U.S. Cl.
CPC ............ *C07D 403/04* (2013.01); *A61P 35/00* (2018.01); *C07D 405/14* (2013.01); *C07D 409/14* (2013.01)

(58) Field of Classification Search
CPC ... C07D 403/04; C07D 405/14; C07D 409/14
See application file for complete search history.

(56) References Cited

PUBLICATIONS

Singh et al., "Effective synthesis of benzimidazoles-imidazo[1,2-a]pyrazine conjugates: A comparative study of mono- and bis-benzimidazoles for antitumor activity", European Journal of Medicinal Chemistry, 180 (2019) 546-561.

El-Shaieb, "Microwave Irradiation Assisted Facile Synthesis of New Imidazole, Pyrazine, and Benzodiazocine Derivatives Using Diaminomaleonitrile", Heteroatom Chemistry, vol. 17, No. 5, 2006, pp. 365-368.

Elumalai et al., "A Green, Scalable, One-Minute Synthesis of Benzimidazoles", Synlett, 2020, 31, 547-552.

Chen et al., "Efficient method for the synthesis of fused benzimidazole-imidazoles via deprotection and cyclization reactions", Tetrahedron, 71 (2015) 8424-8427.

*Primary Examiner* — Laura L Stockton
(74) *Attorney, Agent, or Firm* — Vorys, Sater, Seymour and Pease LLP; Mih Suhn Koh

(57) ABSTRACT

Disclosed is a compound of Formula I or a pharmaceutically acceptable salt thereof, and pharmaceutical composition comprising the same, and use thereof in the treatment of diseases benefiting from the inhibition of autophagic flux and/or chromatin ubiquitination, especially in the treatment of breast cancer.

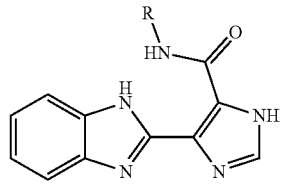

Formula I

17 Claims, 7 Drawing Sheets

BENZIMIDAZOLE DERIVATIVES, PHARMACEUTICAL COMPOSITION COMPRISING THE SAME, AND USE THEREOF

CROSS-REFERENCE TO RELATED APPLICATIONS

The present regular United States patent application claims priority to and the benefits of U.S. Provisional Application No. 63/038,268 filed on Jun. 12, 2020, the entire content of which is hereby incorporated by reference.

TECHNICAL FIELD

The present disclosure relates to benzimidazole derivatives, pharmaceutical composition comprising the same, and use thereof in the treatment of diseases benefiting from the inhibition of autophagic flux and chromatin ubiquitination, especially in the treatment of breast cancer.

BACKGROUND ART

DNA damage can be evoked by a variety of endogenous and exogenous factors, such as reactive oxygen species (ROS) generated during cellular metabolic processes and replication-related errors, as well as ionizing radiation and chemotherapeutic agents. The mammalian cells have evolved multiple repair systems to deal with different types of DNA damage and to keep genomic integrity. The double-strand break (DSB) is generally regarded as the most dangerous form of DNA damage because both strands of DNA are destroyed, the repair is difficult and genetic information may be lost. Fast and accurate transduction of the DNA damage signal is vital to the process of DNA repair. This signal is transduced by a cascade of phosphorylation/dephosphorylation processes. If the DSB was left as misrepaired or unrepaired, it would trigger cell cycle arrest and apoptosis in certain conditions.

Autophagy is a strictly orchestrated and conserved protein degradation pathway by which damaged proteins and organelles are delivered to the lysosome for digestion. It is reported that autophagy consists of three basic types known as microautophagy, chaperon-mediated autophagy (CMA) and macroautophagy which is referred to as "autophagy". The released autophagic products from lysosomes, including fatty acids, amino acids and other molecules, can be reused to offer some energy and nutrients to maintain the survival of cells, especially cancer cells.

Among a variety of cancers, breast cancer (BC) has become the second leading cause of cancer morbidity and mortality among women worldwide. However, TNBC is one of the most aggressive subtypes in breast cancer diagnosed in more than 200,000 women each year and exhibits poor prognosis and high relapse rates at early stages after conventional chemotherapy. Because of its high tolerance to chemotherapy, traditional treatments have been largely ineffective in patients with advanced stages of TNBC. Therefore, it is vital to develop novel therapeutic agents that have the ability to inhibit the proliferation of TNBC cells on the one hand and minimize side effects on the other.

SUMMARY

In the present application, a series of benzimidazole compounds were synthesized, which target the autophagy and DNA damage response (DDR) processes to inhibit the proliferation and growth of cancer cells (such as breast cancer cells), and may combine with other anti-cancer agents to improve the therapy and minimize side effects.

In one aspect, the present application provides a compound of Formula I or a pharmaceutically acceptable salt thereof,

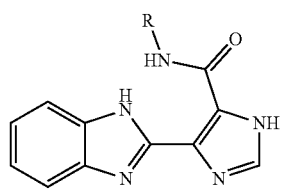

Formula I wherein, R is selected from the group consisting of optionally substituted cycloalkyl, optionally substituted heterocycloalkyl, optionally substituted alkenyl, and optionally substituted alkynyl.

In another aspect, the present application provides a pharmaceutical composition comprising the compound of Formula I or a pharmaceutically acceptable salt thereof.

In still another aspect, the present application provides a method for treating a disease benefiting from the inhibition of autophagic flux and/or chromatin ubiquitination, comprising administering to a subject in need thereof a therapeutically effective amount of a compound of Formula I or a pharmaceutically acceptable salt thereof,

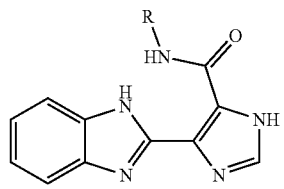

Formula I wherein, R is selected from the group consisting of optionally substituted cycloalkyl, optionally substituted heterocycloalkyl, optionally substituted alkyl, optionally substituted alkenyl, optionally substituted alkynyl, optionally substituted aryl, and optionally substituted heteroaryl.

In a further aspect, the present application provides use of a compound of Formula I or a pharmaceutically acceptable salt thereof in the treatment of a disease benefiting from the inhibition of autophagic flux and/or chromatin ubiquitination,

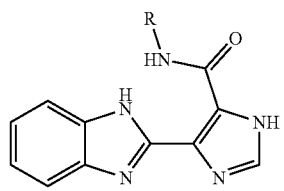

Formula I wherein, R is selected from the group consisting of optionally substituted cycloalkyl, optionally substituted heterocycloalkyl, optionally substituted alkyl, optionally substituted alkenyl, optionally substituted alkynyl, optionally substituted aryl, and optionally substituted heteroaryl.

BRIEF DESCRIPTION OF THE DRAWINGS

FIG. 2A: cell viability was measured with the MTT assay. MDA-MB-231 and MDA-MB-468 cells were exposed to the indicated concentrations of compound 7a for 24, 48 and 72 h. FIGS. 2B and 2C: cell morphology and cell count of MDA-MB-231 and MDA-MB-468 cells were captured with microscope after treating with the indicated concentrations of compound 7a for 48 h. These cells were visualized with the images and quantitated by histogram, Scale bar, 100 µm. FIGS. 2D and 2E: colony formation assay was performed to evaluate TNBC growth in vitro after treatment with the indicated concentrations of compound 7a for 14 days. The colonies were visualized with the images and quantitated by histogram. All data were demonstrated as the mean±SD of three independent experiments. *P<0.05; P<0.01; *P<0.001 versus vehicle.

FIGS. 3A and 3B: Ki67-staining assay was employed to further determine proliferation inhibition after exposure to compound 7a for 48 h. Scale bar, 100 µm. FIGS. 3C and 3D: cell cycle analysis of MDA-MB-231 and MDA-MB-468 cells was measured by flow cytometry in the presence of DMSO vehicle or compound 7a. Graph is representative of percentage mean of three independent experiments. FIG. 3E: impacts of compound 7a on expression level of S-phase related proteins. Cyclin A, cyclin B, P21, CDK1 and CDK2 in MDA-MB-231 and MDA-MB-468 cells were detected by immunoblotting. β-tubulin was used as a loading control. All data were demonstrated as the mean±SD of three independent experiments. *P<0.05; P<0.01; *P<0.001 versus vehicle.

FIG. 4A: MDA-MB-231 and MDA-MB-468 cells were treated with indicated concentrations of compound 7a for 48 h. Then, Cells were harvested and stained with annexin-V/PI. The Q4 (annexin-V−/PI−), Q3 (annexin-V+/PI−) and Q2 (annexin-V+/PI+) quadrants represent the populations of normal, early apoptotic and late apoptotic cells, respectively. FIG. 4B: histograms represent the percentages of surviving cells, early and late apoptotic cells. The data are shown as the means±SD (n=3). FIG. 4C: mitochondria membrane potential was analyzed after treatment with indicated concentrations of compound 7a and staining with JC-1. The stained cells were analyzed by flow cytometric for the determination of $\Delta\Psi m$. FIG. 4D: the corresponding histogram shows the percentages of cells with high $\Delta\Psi m$ (survival) and low $\Delta\Psi m$ (apoptosis). Values represent the means±SD (n=3). *P<0.05; P<0.01; *P<0.001. E. MDA-MB-231 and MDA-MB-468 were treated with indicated concentrations of compound 7a for 48 h, and then expression of intrinsic apoptosis-related proteins such as Bak, Bax, Bim, Bcl-2 and cytochrome c, and cleaved caspase 3, caspase 9 and PARP were measured with western blotting. β-tubulin was used as a loading control. FIG. 4F: MDA-MB-231 and MDA-MB-468 were treated with compound 7a (20 µM) either alone or combination with apoptosis inhibitor Z-VAD-FMK (20 µM) for 48 h, and the percentage of cell viability was detected by MTT assay. *P<0.05; **P<0.01.

FIG. 5A: immunofluorescence was performed in both MDA-MB-231 and MDA-MB-468 cells after the treatment with indicated concentrations of compound 7a. FIG. 5B: LC3B fluorescent puncta was counted and presented in the histogram. FIG. 5C: Western blotting analysis of LC3B and p62 in MDA-MB-231 and MDA-MB-468 cells exposed to the indicated concentrations and times of compound 7a. β-Tubulin was used as a loading control. FIG. 5D: HCT116 cells were stably transfected with mCherry-GFP-LC3 and treated with compound 7a for additional 24 h. Yellow fluorescence indicates the formation of autophagosomes while the red signal represents the acidic autophagolysosomes. Scale bar, 100 µm. FIG. 5E: Quantitative analysis of the autophagosome accumulation of compound 7a-treated cells. Yellow dots were counted in three independent experiments shown in (D). The data are expressed as means±SD (n=3). *P<0.05; **P<0.01 compared with the control group.

FIG. 6A: MDA-MB-231 and MDA-MB-468 were treated with indicated concentrations of compound 7a for 48 h, and then the immunofluorescence analysis was performed to detect γH2AX signal, the histone H2AX phosphorylation representing DSBs. Scale bar: 100 µm. FIG. 6B: γH2AX positive cells in (FIG. 6A) were counted and presented in the histogram. FIGS. 6C and 6D: following treatment with different concentrations (FIG. 6C) and times (FIG. 6D) of compound 7a, treated cell were lysed and phosphorylation/activation levels of ATM, NBS1, SMC1, γH2AX were examined by western blotting. Additionally, RNF8 and DNA repair proteins such as BRCA2 and RAD51 were detected using western. β-tubulin was employed as a loading control. FIGS. 6E and 6F: MDA-MB-231 and MDA-MB-468 cells were treated in the absence or presence of indicated concentrations of compound 7a. P62 signal was measured by immunofluorescence analysis. The nucleus was confirmed with DAPI (4,6-diamidino-2-phenylindole) staining. FIG. 6G: nuclear and cytoplasmic proteins were obtained from MDA-MB-231 and MDA-MB-468 cells treated as in (FIG. 6E). Western blotting was employed to detect the p62 distribution between nucleus and cytoplasm. Histone 4 (H4) represents nuclear proteins while glyceraldehyde-3-phosphate dehydrogenase (GAPDH) indicates cytoplasm proteins. The results were representative of three independent experiments. FIG. 6H: Compound 7a reduced the H2A ubiquitination in a p62 dependent manner. HA-tagged ubiquitin (Ub) was transfected into HEK293T cells, and then cells were treated with 20 NM compound 7a for 24 h. HA-Ub was immunoprecipitated with HA binding beads and ubiquitinated H2A/H2AX was detected with anti-H2A/H2AX. Data are representative of at least three independent experiments.

FIG. 7A: representative photographs of tumors after treatment (Day 45) with vehicle (control) and compound 7a (5 mg/kg and 15 mg/kg). FIGS. 7B and 7C: relative tumor volume (mm$^3$) over time (days) and tumor weight was assessed in MDA-MB-231 xenografts following treatment with compound 7a by intraperitoneal injection (IP). Tumor volume was measured by "V=0.5× W$^2$×L." W=width (mm), L=length (mm). FIGS. 7D and 7E: representative images of hematoxylin and eosin (H&E) staining and immunohistochemistry analysis of Ki67 in MDA-MB-231-induced tumor xenografts, and qualification result (E) of Ki67 positive cells in tumor tissues. FIG. 7F: the expression levels of LC3B-II, p62, γH2AX and cleaved-PARP were detected in the tumors following treatment with vehicle (first three lanes), 5 mg/kg (middle three lanes) and 15 mg/kg (last three lanes) compound 7a. β-tubulin as a loading control. All results are expressed as the mean±SD of three independent experiments, (*p<0.05).

DETAILED DESCRIPTION OF THE INVENTION

Definitions

Figure 1:
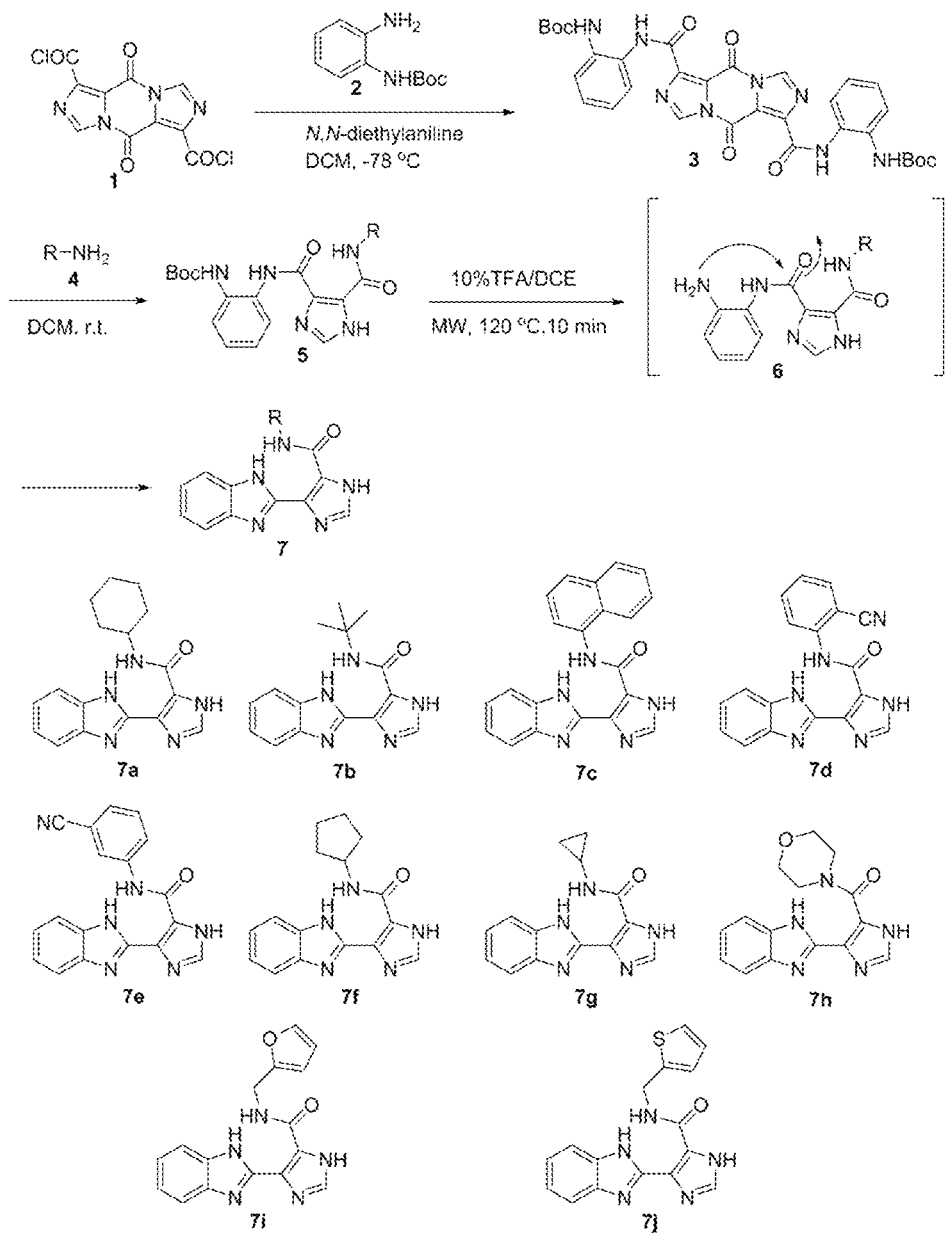
FIG. 1 shows the synthetic strategy of the benzimidazole derivatives of the present application.

Unless stated otherwise, the following terms used herein have the following meanings. A specific term shall not be considered unclear or indefinite when it is not specially defined. It should be understood according to its general meaning. A trade name used herein refers to a corresponding product or an active ingredient thereof.

The term "substituted" means that one or more hydrogen atoms on a given atom are replaced with a substituent, provided that the given atom has a normal valence state and the compound after substitution is stable. When the substituent is an oxo (i.e., =O), which means that two hydrogen atoms are replaced, the oxo substitution will not occur on an aromatic group.

The term "optional" or "optionally" means that the subsequently described event or circumstance may or may not occur, and that the description includes instances where said event or circumstance occurs and instances where said event or circumstance does not occurs. For example, ethyl group is "optionally" substituted with one or more fluorine or chlorine atoms, which means that ethyl group may be unsubstituted ($CH_2CH_3$), mono-substituted (such as $CH_2CH_2F$, $CHClCH_3$), multiple-substituted (such as $CHFCH_2F$, $CHClCHF_2$, $CH_2CHF_2$, and so on) or fully substituted ($CCl_2CF_3$, $CF_2CF_3$). A person skilled in the art will understand that in respect to any group containing one or more substituents, any substitution or substitution mode that is spatially impossible and/or not synthesizable will not be introduced.

The term "optionally substituted" as used herein means that a group can be optionally substituted by one or more substituents independently selected from the group consisting of alkyl, alkenyl, halo, haloalkyl, haloalkenyl, alkoxy, alkylthio, cyano, nitro, hydroxy, mercapto, —C(=S)OH, —C(=S)O-alkyl, —C(=S)—H, —C(=S)-alkyl, aryl, aryloxy, aralkyl, cycloalkyl, cycloalkyloxy, cycloalkylalkyl, cycloalkenyl, cycloalkenyloxy, cycloalkenylalkyl, heterocycloalkyl, heterocycloalkyloxy, heterocycloalkylalkyl, heteroaryl, heteroaryloxy, heteroarylalkyl, hydroxyamino, alkoxyamino, —OC(O)—$R^1$, —N($R^1$)$_2$, —N$R^1R^2$, —C(=O)$R^1$, —C(O)O$R^1$, —C(O)N($R^1$)$_2$, —N($R^1$)C(O)O$R^2$, —N($R^1$)C(=O)$R^2$, —N(R')C(=O)R', —N($R^1$)C(=O)$R^1$, —N($R^1$)(S(O)$_t$$R^2$) (wherein t is 1 or 2), —S(O)$_t$O$R^2$ (wherein t is 1 or 2), —S(=O)$_t$$R^1$ (wherein t is 0, 1, or 2), —S(O)$_t$N($R^1$)$_2$ (wherein t is 1 or 2), and —(CH$_2$)$_t$P(=O)(O$R^1$)$_2$ (wherein t is 0, 1, or 2) such as —P(=O)(O$R^1$)$_2$, —P(=O)(OH)$_2$, —CH$_2$P(=O)(O$R^1$)$_2$, and —CH$_2$P(=O)(OH)$_2$, wherein each $R^1$ and each $R^2$ are independently hydrogen, alkyl, alkenyl, alkynyl, cycloalkyl, cycloalkenyl, aryl, arylalkyl, heterocycloalkyl, heterocycloalkylalkyl, heteroaryl, or heteroarylalkyl, each of which is optionally substituted by halo, —CN, —NO$_2$, —NH$_2$, —NHCH$_3$, —NHCH$_2$CH$_3$, oxo, —OH, —OCH$_3$ or 3- to 6-membered heterocyclyl.

The expression $C_{m-n}$ as used herein means that this moiety has an integer number of carbon atoms within a given range. For example, "$C_{1-6}$" means that this group may have 1 carbon atom, 2 carbon atoms, 3 carbon atoms, 4 carbon atoms, 5 carbon atoms or 6 carbon atoms.

When any variant (such as, R) occurs more than one times at the composition or structure of a compound, it is defined independently in each case. Therefore, for example, if a group is substituted with two Rs, then each R has an independent option.

The term "halogen" or "halo" refers to fluoro, chloro, bromo and iodo.

The term "hydroxy" refers to —OH group.

The term "cyano" refers to —CN group.

The term "amino" refers to —NH$_2$ group.

The term "nitro" refers to —NO$_2$ group. The term "alkyl" refers to a hydrocarbyl group of Formula $C_nH_{2n+1}$. The alkyl group can be straight or branched. For example, the term "$C_{1-6}$ alkyl" refers to an alkyl group having 1 to 6 carbon atoms, such as 1 carbon atom, 2 carbon atoms, 3 carbon atoms, 4 carbon atoms, 5 carbon atoms and 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) in an alkoxy group, a monoalkylamino group, a dialkylamino group, an alkylsulfonyl group, an alkoxycarbonyl group, and an alkylthio group has the same definition as defined above.

The term "ester group" refers to —COO$R^{13}$ group, wherein $R^{13}$ is alkyl as defined above.

The term "alkenyl" refers to a linear or branched unsaturated aliphatic hydrocarbyl group consisting of carbon and hydrogen atoms, which has at least one carbon carbon double bond. For example, $C_2$, $C_3$, $C_4$, $C_5$, $C_6$, $C_7$, $C_8$, $C_9$, $C_{10}$, $C_{11}$, $C_{12}$, $C_{13}$ $C_{14}$, $C_{15}$, $C_{16}$, $C_{17}$, $C_{18}$, $C_{19}$, or $C_{20}$ alkenyl.

The term "alkynyl" refers to a linear or branched unsaturated aliphatic hydrocarbyl group consisting of carbon and hydrogen atoms, which has at least one carbon carbon triple bond. For example, $C_2$, $C_3$, $C_4$, $C_5$, $C_6$, $C_7$, $C_8$, $C_9$, $C_{10}$, $C_{11}$, $C_{12}$, $C_{13}$ $C_{14}$, $C_{15}$, $C_{16}$, $C_{17}$, $C_{18}$, $C_{19}$, or $C_{20}$ alkynyl.

The term "alkoxy" refers to —O-alkyl.

The term "cycloalkyl" refers to an all-carbon ring that is fully saturated and can exist in the form of a monocyclic ring, bicyclic ring, tricyclic ring, or polycyclic ring, fused ring, bridged ring or spirocyclic ring. Unless otherwise indicated, the carbocycle is typically a 3- to 10-membered ring, such as 3-membered ring, 4-membered ring, 5-membered ring, 6-membered ring, 7-membered ring, 8-membered ring, 9-membered ring, and 10-membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl etc.

The term "heterocycloalkyl" refers to a fully saturated or partially unsaturated (but not fully unsaturated heteroaromatic) non-aromatic ring that can be exist in the form of a monocyclic ring, bicyclic ring, tricyclic ring, or polycyclic ring, fused ring, bridged ring or spirocyclic ring. Unless otherwise indicated, the heterocycloalkyl is typically a 3- to 10-membered ring (such as 3-membered ring, 4-membered ring, 5-membered ring, 6-membered ring, 7-membered ring, 8-membered ring, 9-membered ring, and 10-membered ring) containing 1 to 4 heteroatoms (such as 1, 2, 3 or 4 heteroatoms) independently selected from sulfur, oxygen, and/or nitrogen. Non-limiting examples of heterocycloalkyl include, but are not limited to oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl, etc.

Unless otherwise specified, the term "heterocyclyl" or specific terms thereof (such as heteroaryl, heterocycloalkyl, heterocycloalkenyl, and heterocycloalkynyl) themself or combining with other terms respectively represent a cyclic "heterohydrocarbyl". In addition, in the term "heterocyclyl", heteroatoms may occupy the position where the heterocyclic ring is attached to the rest part of the molecule. Non-limited examples of heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophen-2-yl, tetrahydrothiophen-3-yl, 1-piperazinyl and 2-piperazinyl.

The term "aryl" refers to a group of an all-carbon monocyclic or fused polycyclic aromatic ring having a conjugated π-electron system. For example, an aryl may have 6 to 20, 6 to 14, or 6 to 12 carbon atoms. Aryl may have at least one aromatic ring, and non-limiting examples thereof include, but are not limited to, phenyl, naphthyl, anthryl and 1,2,3,4-tetrahydronaphthalene, etc.

The term "heteroaryl" refers to a monocyclic or fused polycyclic system containing at least one ring atom (such as 1, 2, 3, 4 or 5 ring atoms) selected from N, O, and S with remaining ring atoms being C, and having at least one aromatic ring. Preferred heteroaryl has a single 4- to 8-membered ring (such as 4-membered ring, 5-membered ring, 6-membered ring, 7-membered ring, or 8-membered ring), especially single 5- to 8-membered ring, or has a fused polycyclic ring containing 6 to 14 (such as 6-membered ring, 7-membered ring, 8-membered ring, 9-membered ring, 10-membered ring, 11-membered ring, 12-membered ring, 13-membered ring, and 14-membered ring), especially 6 to 10 rings atoms. Non-limiting examples of heteroaryl include, but are not limited to, pyrrolyl, furyl, thienyl, thiazolyl imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

The term "treatment" or "treating" refers to the administration of the compounds or preparations of the present application for ameliorating or eliminating diseases or one or more symptoms associated with the diseases, comprising:

(i) inhibition of diseases or conditions, i.e. restraining their development; or (ii) relief of diseases or conditions, i.e. recovering from the diseases or conditions.

The term "therapeutically effective amount" means an amount of a compound of the present application that (i) treats or prevents a particular disease, condition, or disorder, (ii) attenuates, ameliorates, or eliminates one or more symptoms of a particular disease, condition, or disorder, or (iii) prevents or retards the onset of one or more symptoms of a particular disease, condition, or disorder as described herein. The amount of the compounds of the present application constituting so-called "therapeutically effective amount" depends on the compound, disease condition and severity thereof, the way of administration and age of the mammal to be treated, but can be routinely determined by those skilled in the art on the basis of their knowledge and the disclosure herein.

The term "pharmaceutical composition" refers to a formulation, which comprises one or more compounds of the present application, or the salts thereof, along with the carriers, excipients and/or media generally accepted in the field for delivering the biologically active compounds to the organisms (such as humans). The purpose of pharmaceutical composition is to facilitate the administration of the compound of the present application to the organisms.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The term "pharmaceutically acceptable salt" includes, but is not limited to, an acid addition salt formed from the compound of Formula I and an inorganic acid, an acid addition salt formed from the compound of Formula I and an organic acid, or an addition salt formed from the compound of Formula I and an acidic amino acid, etc. The term "pharmaceutical composition" refers to a mixture of one or more compounds of the present application or pharmaceutically acceptable salts thereof and a pharmaceutically acceptable excipient. The purpose of pharmaceutical composition is to facilitate the administration of the compounds of the present application to the organism.

The term "pharmaceutically acceptable carrier" refers to those carriers which have no significant irritation and do not impair the bioactivity and property of the active compound. The "pharmaceutically acceptable carrier" refers to inert substance which is administered with active ingredient and is beneficial to the administration thereof, and comprises but not limited to any of the following substances approved by State Food and Drug Administration for use in human or animal (e.g. livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference.

The term "excipient" generally refers to the carrier, diluent and/or medium used to formulate effective pharmaceutical composition.

The pharmaceutical composition of the present application can be prepared through combining the compounds of the present application and suitable pharmaceutical acceptable carriers or excipients. For example, it can be prepared as solid, semi-solid, liquid or gaseous formulations, such as tablets, pills, capsules, powder, granules, ointments, emulsions, suspensions, solutions, suppositories, injections, inhalants, gels, microspheres and aerosol, etc.

The typical routes for the administration of the compounds of the present application or the pharmaceutically acceptable salts thereof or the pharmaceutical composition thereof include, but are not limited to oral, rectal, transmucosal, enteral administration, or topical, percutaneous, inhalational, parenteral, sublingual, intravaginal, intranasal, intraocular, intraperitoneal, intramuscular, subcutaneous, intravenous administration. The preferred administration route is oral administration.

The pharmaceutical composition of the present application can be manufactured through the well-known methods in the art, such as the mix, dissolving, granulation, sugar coating, grinding, emulsification, freeze-drying, etc.

In an embodiment, the pharmaceutical composition is in the form for oral use. For oral administration, the active compounds can be mixed with the pharmaceutically acceptable carriers known in the art, to prepare the pharmaceutical composition. With these carriers, the compounds of the present application can be formulated into tablets, pills, lozenges, sugar-coated tablets, capsules, liquid, gels, syrup, suspensions and the like, for oral administration to the patients.

The solid oral use composition can be prepared through conventional mixing, filling or compressing methods. For example, it can be obtained through the following method: the active compounds are mixed with the solid excipients; optionally the resulting mixture is ground, and other suitable adjuvants are added if necessary; then the mixture is processed into granules, so that the core of the tablets or sugar-coated tablets is obtained. Suitable adjuvants include, but are not limited to, adhesives, diluents, disintegrants, lubricants, glidants, sweeteners or flavoring agents, etc., such as microcrystalline cellulose, glucose solution, mucilage of gum arabic, gelatin solution, sucrose and starch paste; talc, starch, magnesium stearate, calcium stearate or stearic acid; lactose, sucrose, starch, mannitol, sorbitol or dicalcium phosphate; silica; crosslinked sodium carboxymethylcellulose, pre-gelatinized starch, sodium starch glycolate, alginic acid, corn starch, potato starch, methyl cellulose, agar, carboxymethyl cellulose, crosslinked polyvinylpyrrolidone, etc. Optionally, the core of the tablet can be coated through the well-known methods in general pharmaceutical practice, and enteric coating is particularly used.

The pharmaceutical composition is also suitable for parenteral administration, such as sterile solutions, suspensions or freeze-dried products in adequate unit dose form. The suitable excipients, such as fillers, buffers or surfactants, can also be used.

In all the methods for applying the compound of Formula I according to the disclosure, the daily administered dosage is, for example, 0.01-200 mg/kg body weight.

The phrase "comprise" and English variations thereof, such as "comprises" and "comprising", should be construed in an open and inclusive sense, that is as, "including, but not limited to".

In one aspect, the present application provides a compound of Formula I or a pharmaceutically acceptable salt thereof,

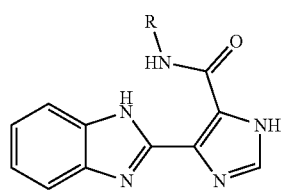

Formula I wherein, R is selected from the group consisting of optionally substituted cycloalkyl, optionally substituted heterocycloalkyl, optionally substituted alkenyl, and optionally substituted alkynyl.

In some embodiments, R is selected from the group consisting of cycloalkyl, heterocycloalkyl, alkenyl, and alkynyl, each of which is independently optionally substituted with one or more substituents independently selected from the group consisting of halo, alkyl, $-N(R^1)_2$, $-NR^1R^2$, $-S(=O)R^1$, $-S(=O)_2R^1$, $-C(=O)R^1$, $-N(R^1)C(=O)R^2$, $-N(R^1)C(=O)R^1$, and $-(CH_2)_tP(=O)(OR^1)_2$ wherein t is 0, 1, or 2;

wherein each $R^1$ and each $R^2$ are independently alkyl, alkenyl, alkynyl, and heterocyclyl, each of which is optionally substituted by halo, $-CN$, $-NO_2$, $-NH_2$, $-NHCH_3$, $-NHCH_2CH_3$, oxo, $-OH$, $-OCH_3$ or 3- to 6-membered heterocyclyl.

In some embodiments, R is selected from the group consisting of optionally substituted $C_{3-20}$ cycloalkyl, optionally substituted 3- to 20-membered heterocycloalkyl, optionally substituted $C_{2-20}$ alkenyl, and optionally substituted $C_{2-20}$ alkynyl.

In some embodiments, R is selected from the group consisting of optionally substituted $C_{3-15}$ cycloalkyl, optionally substituted 3- to 15-membered heterocycloalkyl, optionally substituted $C_{2-15}$ alkenyl, and optionally substituted $C_{2-15}$ alkynyl.

In some embodiments, R is selected from the group consisting of optionally substituted $C_{3-12}$ cycloalkyl, optionally substituted 3- to 12-membered heterocycloalkyl, optionally substituted $C_{2-10}$ alkenyl, and optionally substituted $C_{2-10}$ alkynyl.

In some embodiments, R is 3- to 8-membered cycloalkyl or 5- to 6-membered heterocycloalkyl.

In some embodiments, the compound of Formula I or a pharmaceutically acceptable salt thereof is selected from:

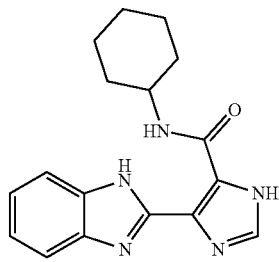

7a

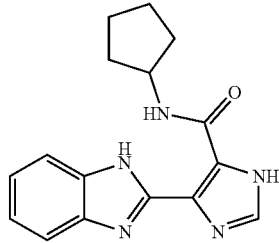

7f

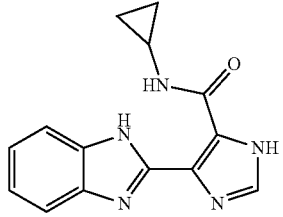

7g

-continued

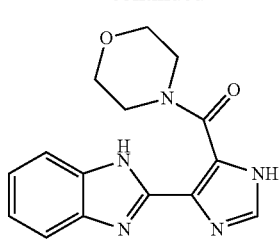

7h or a pharmaceutically acceptable salt thereof.

In another aspect, the present application provides a pharmaceutical composition comprising the compound of Formula I or a pharmaceutically acceptable salt thereof.

In some embodiments, the pharmaceutical composition further comprises one or more pharmaceutically acceptable carriers or excipients.

In still another aspect, the present application provides a method for treating a disease benefiting from the inhibition of autophagic flux and/or chromatin ubiquitination, comprising administering to a subject in need thereof a therapeutically effective amount of a compound of Formula I or a pharmaceutically acceptable salt thereof,

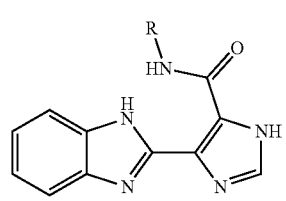

Formula I wherein, R is selected from the group consisting of optionally substituted cycloalkyl, optionally substituted heterocycloalkyl, optionally substituted alkyl, optionally substituted alkenyl, optionally substituted alkynyl, optionally substituted aryl, and optionally substituted heteroaryl.

In some embodiments, R is selected from the group consisting of cycloalkyl, heterocycloalkyl, alkyl, alkenyl, alkynyl, aryl, and heteroaryl, each of which is independently optionally substituted with one or more substituents independently selected from the group consisting of halo, alkyl, haloalkyl, cyano, aryl, alkoxy, alkoxyaryl, heteroaryl, ester group, —N(R$^1$)$_2$, —NR$^1$R$^2$, —S(=O)R$^1$, —S(=O)$_2$R$^1$, —C(=O)R$^1$, —N(R$^1$)C(=O)R$^2$, —N(R$^1$)C(=O)R$^1$, and —(CH$_2$)$_t$P(=O)(OR$^1$)$_2$ wherein t is 0, 1, or 2;

wherein each R$^1$ and each R$^2$ are independently alkyl, alkenyl, alkynyl, and heterocyclyl, each of which is optionally substituted by halo, —CN, —NO$_2$, —NH$_2$, —NHCH$_3$, —NHCH$_2$CH$_3$, oxo, —OH, —OCH$_3$ or 3- to 6-membered heterocyclyl.

In some embodiments, R is selected from the group consisting of optionally substituted C$_{3-20}$ cycloalkyl and optionally substituted 3- to 20-membered heterocycloalkyl, optionally substituted C$_{1-20}$ alkyl, optionally substituted C$_{2-20}$ alkenyl, optionally substituted C$_{2-20}$ alkynyl, optionally substituted C$_{6-20}$ aryl, and optionally substituted 5- to 20-membered heteroaryl.

In some embodiments, R is selected from the group consisting of optionally substituted C$_{3-15}$ cycloalkyl and optionally substituted 3- to 15-membered heterocycloalkyl, optionally substituted C$_{1-15}$ alkyl, optionally substituted C$_{2-15}$ alkenyl, optionally substituted C$_{2-15}$ alkynyl, optionally substituted C$_{6-15}$ aryl, and optionally substituted 5- to 15-membered heteroaryl.

In some embodiments, R is selected from the group consisting of optionally substituted C$_{3-12}$ cycloalkyl and optionally substituted 3- to 12-membered heterocycloalkyl, optionally substituted C$_{1-10}$ alkyl, optionally substituted C$_{2-10}$ alkenyl, optionally substituted C$_{2-10}$ alkynyl, optionally substituted C$_{6-12}$ aryl, and optionally substituted 5- to 12-membered heteroaryl.

In some embodiments, R is 3- to 8-membered cycloalkyl or 5- to 6-membered heterocycloalkyl.

In some embodiments, the compound of Formula I or a pharmaceutically acceptable salt thereof is selected from:

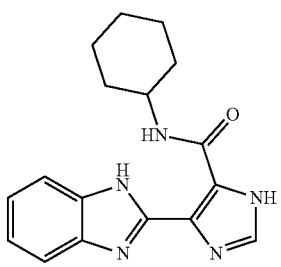

7a

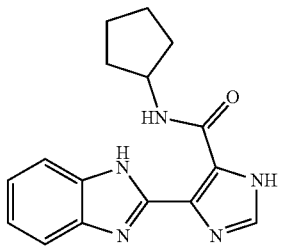

7f

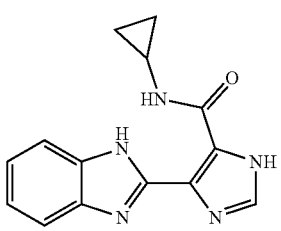

7g

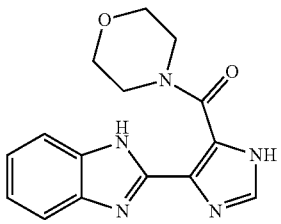

7h or a pharmaceutically acceptable salt thereof.

In some embodiments, the disease is breast cancer.

In some embodiments, the breast cancer is triple negative breast cancer.

In a further aspect, the present application provides use of a compound of Formula I or a pharmaceutically acceptable salt thereof in the treatment of a disease benefiting from the inhibition of autophagic flux and/or chromatin ubiquitination,

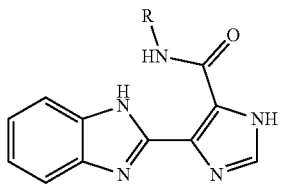

Formula I wherein, R is selected from the group consisting of optionally substituted cycloalkyl, optionally substituted heterocycloalkyl, optionally substituted alkyl, optionally substituted alkenyl, optionally substituted alkynyl, optionally substituted aryl, and optionally substituted heteroaryl.

In some embodiments, R is selected from the group consisting of cycloalkyl, heterocycloalkyl, alkyl, alkenyl, alkynyl, aryl, and heteroaryl, each of which is independently optionally substituted with one or more substituents independently selected from the group consisting of halo, alkyl, haloalkyl, cyano, aryl, alkoxy, alkoxyaryl, heteroaryl, ester group, —N(R$^1$)$_2$, —NR$^1$R$^2$, —S(=O)R$^1$, —S(=O)$_2$R$^1$, —C(=O)R$^1$, —N(R$^1$)C(=O)R$^2$, —N(R$^1$)C(=O)R$^1$, and —(CH$_2$)$_t$P(=O)(OR$^1$)$_2$ wherein t is 0, 1, or 2;

wherein each R$^1$ and each R$^2$ are independently alkyl, alkenyl, alkynyl, and heterocyclyl, each of which is optionally substituted by halo, —CN, —NO$_2$, —NH$_2$, —NHCH$_3$, —NHCH$_2$CH$_3$, oxo, —OH, —OCH$_3$ or 3- to 6-membered heterocyclyl.

In some embodiments, R is selected from the group consisting of optionally substituted C$_{3-20}$ cycloalkyl and optionally substituted 3- to 20-membered heterocycloalkyl, optionally substituted C$_{1-20}$ alkyl, optionally substituted C$_{2-20}$ alkenyl, optionally substituted C$_{2-20}$ alkynyl, optionally substituted C$_{6-20}$ aryl, and optionally substituted 5- to 20-membered heteroaryl.

In some embodiments, R is selected from the group consisting of optionally substituted C$_{3-15}$ cycloalkyl and optionally substituted 3- to 15-membered heterocycloalkyl, optionally substituted C$_{1-15}$ alkyl, optionally substituted C$_{2-15}$ alkenyl, optionally substituted C$_{2-15}$ alkynyl, optionally substituted C$_{6-15}$ aryl, and optionally substituted 5- to 15-membered heteroaryl.

In some embodiments, R is selected from the group consisting of optionally substituted C$_{3-12}$ cycloalkyl and optionally substituted 3- to 12-membered heterocycloalkyl, optionally substituted C$_{1-10}$ alkyl, optionally substituted C$_{2-10}$ alkenyl, optionally substituted C$_{2-10}$ alkynyl, optionally substituted C$_{6-12}$ aryl, and optionally substituted 5- to 12-membered heteroaryl.

In some embodiments, R is 3- to 8-membered cycloalkyl or 5- to 6-membered heterocycloalkyl.

In some embodiments, the compound of Formula I or a pharmaceutically acceptable salt thereof is selected from:

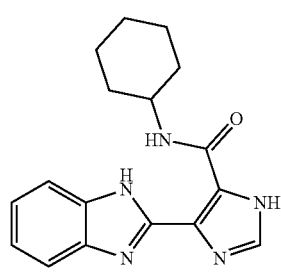

7a

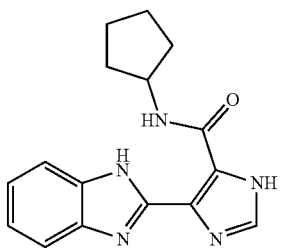

7f

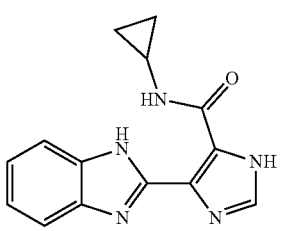

7g

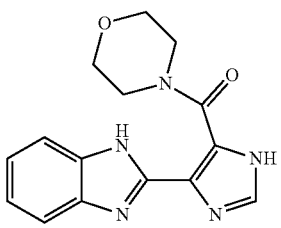

7h or a pharmaceutically acceptable salt thereof.

In some embodiments, the disease is breast cancer.

In some embodiments, the breast cancer is triple negative breast cancer (TNBC).

In another aspect, the present application provides use of the compound of Formula I or a pharmaceutically acceptable salt thereof in the manufacture of a medicament for the treatment of a disease benefiting from the inhibition of autophagic flux and/or chromatin ubiquitination. In some embodiments, the disease is breast cancer. In some embodiments, the breast cancer is triple negative breast cancer (TNBC).

In a further aspect, the present application provides the compound of Formula I or a pharmaceutically acceptable salt thereof according to the present application for use in the treatment of a disease benefiting from the inhibition of autophagic flux and/or chromatin ubiquitination. In some embodiments, the disease is breast cancer. In some embodiments, the breast cancer is triple negative breast cancer (TNBC).

Herein, a serial of benzimidazole derivatives were synthesized and their effect on TNBC was investigated. The benzimidazole derivatives of the present application are able to inhibit cancer cell proliferation in vitro/vivo, promote apoptosis, induce p62 accumulation due to blockage of the fusion between autophagosome and lysosome, and initiate DNA damage. Upregulation of p62 induced by the benzimidazole derivatives of the present application in human TNBC results in deficiency of DNA repair because of H2A ubiquitination decrease leading to the reduced recruitment of DNA repair-related proteins to DNA damage foci.

The present application develops effective novel agents regulating the core molecular pathway of TNBC such as autophagy and DNA damage response. The benzimidazole derivative compounds of the present application have an activity in suppressing proliferation of TNBC cells, they can induce mitochondria-mediated apoptosis and cell cycle arrest at S-phase. Furthermore, they initiate autophagy while suppressed fusion of autophagosome and lysosome, leading to p62 accumulation in the nucleus. The impaired autophagic flux results in DNA damage and DNA damage response by triggering phosphorylation of ATM, H2AX and SMC1 whereas decrease DNA repair. Mechanistically, RNF8, an E3 ligase essential for chromatin ubiquitination, is significantly reduced due to p62 accumulation after treatment with the compounds of the present application. As a result, histone H2A ubiquitination is remarkably suppressed in TNBC cells, resulting in DNA repair-related proteins including RAT51 and BRCA2 cannot be recruited to the sites of DNA double-strand breaks (DSBs). Moreover, The treatment with the compounds of the present application exerts a significant in vivo anti-tumor activity in MDA-MB-231 xenograft model. Together, The data in the present application suggests that autophagic flux-deficiency induced p62 accumulation due to the treatment with the compounds of the present application leads to inhibition of histone ubiquitination, and then results in the recruitment loss of DNA repair-related proteins to DSBs sites, implying that the compounds of the present application increases genome instability by a unique mechanism and has application prospect for TNBC treatment in clinic.

Unless indicated otherwise, the abbreviations used herein have the following meanings.

BC: breast cancer; TNBC: triple negative breast cancer; ATCC: American Type Culture Collection; CST: Cell Signaling Technology; DMEM: Dulbecco's modified eagle medium; FBS: fetal bovine serum; PBS: phosphate buffer saline; DMSO: dimethyl sulfoxide; PFA: paraformaldehyde; MTT: 3-(4,5-dimethyl-2-thiazolyl)-2,5-diphenyl-2-H-tetrazolium bromide; Brdu: 5-bromo-2'-deoxyuridine; DAPI: 4',6-diamidino-2-phenylindole; FACS: fluorescence activated cell sorting; FITC: fluorescein isothiocyanate; PI: propidium iodide; RIPA: radio immunoprecipitation assay; SDS-PAGE: sodium dodecyl sulfate polyacrylamide gel electrophoresis; PVDF: polyvinylidene difluoride; TBST: tris-buffered saline with Tween-20; BSA: bovine serum albumin; SD: standard deviation; CDKs: cyclin-dependent kinases; BAX: Bcl-2 associated X protein; BCL-2: B-cell lymphoma-2; PARP: poly ADP-ribose polymerase; GAPDH: glyceraldehyde-3-phosphate dehydrogenase; DNA: deoxyribonucleic acid; HR: homologous recombination; NHEJ: non-homologous end joining; DSB: double-strand break; ATM: ataxia telangiectasia mutated; ATR: ataxia telangiectasia mutated and Rad-related protein; NBS1: Nijmegen breakage syndrome; SMC1: structural maintenance of chromosomes 1; CHK1, 2: Checkpoint kinase 1 and 2; BRCA2: breast cancer type 2 susceptibility protein; DR: DNA repair; DDR: DNA damage response; H&E: hematoxylin and eosin staining; $IC_{50}$: 50% inhibitory concentration.

The compound of formula I can be prepared by a person skilled in the field of organic synthesis with standard procedures according to the following scheme:

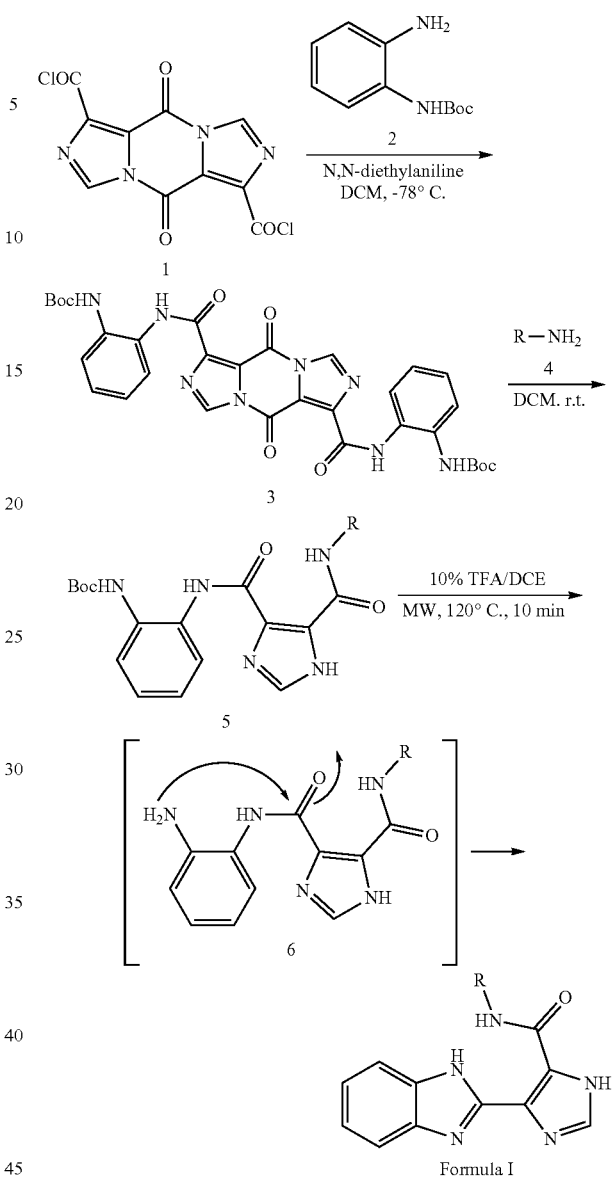

wherein R is as defined in the above.

The compounds of Formula I are prepared by using imidazole-4,5-dicarboxamides (I45DCs) as starting materials with three procedures reaction in mild conditions. To a solution of acid chloride and N,N-diethylaniline in DCM at −78° C. is added N-Boc-1,2-phenylenediamine. The mixture is kept for 1 h at this temperature and then heated to room temperature. After stirring 5 h, the yellow solid is precipitated out from the solvent and filtered to give compound 3 in 92% yield. Then, the mixture of compound 3 and amine in DCM are stirred at room temperature overnight. The solvent is removed and 10% TFA/DCE is added to the residue. In order to deprotect the Boc group, the reaction is treated by microwave irradiation.

EXAMPLES

The purpose of the following specific examples is to facilitate those skilled in the art to more clearly understand and implement the present application. They should not be construed as limiting the scope of the present application, and they are merely exemplary illustrations and typical representatives of the present application.

Preparation Example 1: The Synthesis of Compound 7a

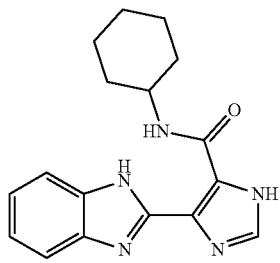

7a

To a suspension of acid chloride compound 1 (1.56 g, 5.0 mmol) and N,N-diethylaniline (1.60 mL, 10 mmol) in DCM (40 mL) at −78° C. was added N-Boc-1,2-phenylenediamine compound 2 (1.04 g, 5.0 mmol). The reaction was kept for 1 h at this temperature and then heated to room temperature. After stirring 5 h, the yellow solid was precipitated out from the solvent and filtered to give compound 3 in 92% yield.

To a suspension of compound 3 (66 mg, 0.1 mmol) in DCM (3 mL) was added amine (0.21 mmol), and stirred at room temperature overnight. Then, the solvent was removed and 10% TFA/DCE (3 mL) was added to the residue. The mixture was treated with microwave at 120° C. for 10 min. After the microwave vial was cooled to room temperature, the solvent was removed under reduced pressure and then diluted with EtOAc (15 mL) and washed with saturated aqueous $Na_2CO_3$ solution and brine. The organic layer was dried over $MgSO_4$ and concentrated. The residue was purified by silica gel column chromatography using a gradient of ethyl acetate/hexane (20-100%) to afford the title compound 7a. $^1$H NMR (400 MHz, DMSO-$d_6$) δ 13.18 (s, 1H), 13.00 (s, 1H), 12.20 (s, 1H), 7.95 (s, 1H), 7.62 (d, J=7.9 Hz, 1H), 7.54 (d, J=6.6 Hz, 1H), 7.30-7.21 (m, 2H), 4.02 (s, 1H), 1.92-1.84 (m, 4H), 1.64-1.41 (m, 6H). $^{13}$C NMR (100 MHz, DMSO-$d_6$) δ 56.80, 147.34, 141.35, 136.65, 133.09, 129.05, 125.66, 122.42, 121.57, 117.27, 111.29, 46.52, 31.35, 24.89, 22.89. HRMS (ESI) m/z calcd for $C_{17}H_{20}N_5O^+$ $(M+H)^+$ 310.16679, found 310.16678.

Interestingly, the formula weight of target compound 7a was founded with a small peak, while higher temperature and longer reaction time provided better yield of target compound 7a.

Preparation Example 2: The Synthesis of Compounds 7b-7j

The compounds 7b-7j were synthesized with reference to the preparation of Compound 7a in the preparation Example 1.

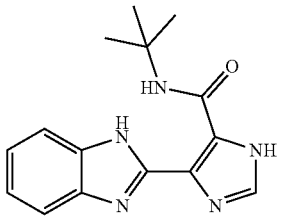

7b

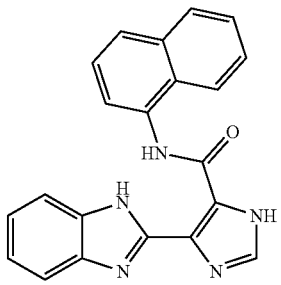

7c

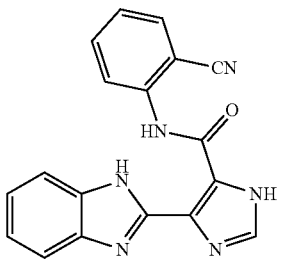

7d

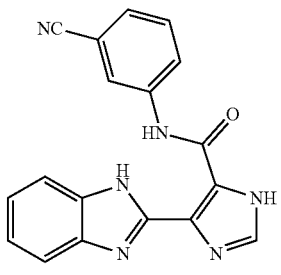

7e

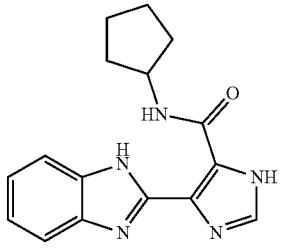

7f

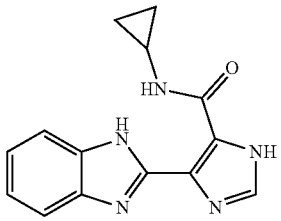

7g

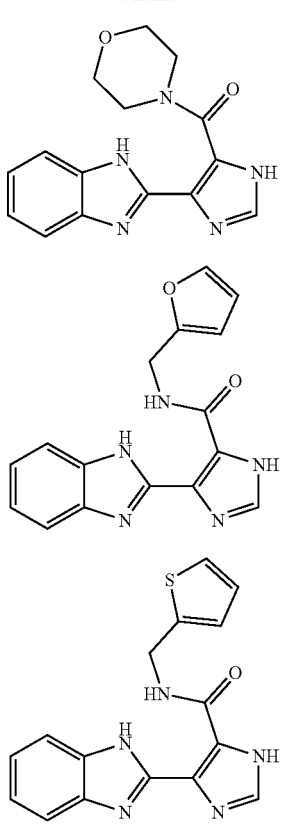

Compound 7b. $^1$H NMR (400 MHz, DMSO-d$_6$) δ 13.09 (s, 1H), 12.99 (s, 1H), 12.14 (s, 1H), 7.93 (s, 1H), 7.57 (d, J=15.3 Hz, 2H), 7.24 (d, J=5.0 Hz, 2H), 1.53 (s, 9H). $^{13}$C NMR (100 MHz, DMSO-d$_6$)$^{13}$C NMR (100 MHz, DMSO) δ 157.04, 147.42, 141.24, 136.39, 133.06, 128.65, 126.49, 122.36, 121.52, 117.24, 111.29, 50.47, 27.88. HRMS (ESI) m/z calcd for C$_{15}$H$_{18}$N$_5$O$^+$ (M+H)$^+$ 284.15114, found 284.15109.

Compound 7c. $^1$H NMR (400 MHz, DMSO-d$_6$) δ 14.18 (s, 1H), 8.67 (d, J=5.2 Hz, 1H), 8.21 (d, J=7.4 Hz, 1H), 8.16 (s, 1H), 8.08-8.02 (m, 1H), 7.84 (d, J=8.1 Hz, 1H), 7.66-7.63 (m, 2H), 7.60 (d, J=7.3 Hz, 3H), 7.31-7.29 (m, 2H). $^{13}$C NMR (100 MHz, DMSO-d$_6$) δ 157.90, 157.52, 157.06, 146.76, 137.81, 133.34, 133.16, 127.86, 126.40, 125.67, 125.21, 124.28, 122.51, 122.18, 119.79. HRMS (ESI) m/z calcd for C$_{21}$H$_{16}$N$_5$O$^+$ (M+H)$^+$ 354.13549, found 354.13574.

Compound 7d. $^1$H NMR (400 MHz, DMSO-d6) δ 15.00 (s, 1H), 13.59 (s, 1H), 13.25 (s, 1H), 8.14 (s, 1H), 8.02 (d, J=8.2 Hz, 1H), 7.94 (d, J=6.6 Hz, 1H), 7.81-7.75 (m, 2H), 7.57 (d, J=7.4 Hz, 1H), 7.42 (t, J=7.7 Hz, 1H), 7.30-7.24 (m, 2H). $^{13}$C NMR (100 MHz, DMSO-d$_6$) δ 156.66, 146.67, 140.82, 139.87, 138.20, 133.30, 133.04, 130.60, 124.83, 124.54, 122.71, 121.68, 118.24, 116.46, 111.34, 105.11. HRMS (ESI) m/z calcd for C$_{18}$H$_{13}$N$_6$O$^+$ (M+H)$^+$ 329.11508, found 329.11447.

Compound 7e. $^1$H NMR (400 MHz, DMSO-d$_6$) δ 15.06 (s, 1H), 13.54 (s, 1H), 13.28 (s, 1H), 8.51 (s, 1H), 8.12 (s, 1H), 8.08 (d, J=8.2 Hz, 1H), 7.89 (d, J=4.3 Hz, 1H), 7.72 (t, J=7.9 Hz, 1H), 7.64-7.59 (m, 2H), 7.34-7.32 (m, 2H). $^{13}$C NMR (100 MHz, DMSO-d$_6$) δ 156.56, 147.06, 140.83, 139.66, 138.08, 133.02, 130.21, 126.61, 125.10, 123.22, 122.94, 121.98, 118.19, 117.52, 111.56. HRMS (ESI) m/z calcd for C$_{18}$H$_{13}$N$_6$O$^+$ (M+H)$^+$ 329.11508, found 329.11511.

Compound 7f. $^1$H NMR (400 MHz, DMSO-d$_6$) δ 13.20 (s, 1H), 13.01 (s, 1H), 12.29 (s, 1H), 7.96 (s, 1H), 7.75-7.46 (m, 2H), 7.27 (d, J=3.7 Hz, 2H), 4.38 (s, 1H), 1.94 (d, J=26.3 Hz, 4H), 1.73 (s, 4H). $^{13}$C NMR (100 MHz, DMSO-d6) δ 157.04, 147.41, 141.29, 136.64, 133.09, 129.05, 125.72, 122.45, 121.63, 117.22, 111.33, 50.32, 32.13, 22.77. HRMS (ESI) m/z calcd for C$_{16}$H$_{18}$N$_5$O$^+$ (M+H)$^+$ 296.15114, found 296.15048.

Compound 7g. $^1$H NMR (400 MHz, DMSO-d$_6$) δ 13.27 (s, 1H), 13.03 (s, 1H), 12.40 (s, 1H), 7.98 (s, 1H), 7.66-7.54 (m, 2H), 7.26 (d, J=5.9 Hz, 2H), 3.01 (d, J=3.2 Hz, 1H), 0.95-0.67 (m, 4H). $^{13}$C NMR (100 MHz, DMSO-d6) δ 160.01, 148.34, 142.18, 137.85, 134.07, 130.29, 126.44, 123.55, 122.68, 118.50, 112.35, 23.13, 6.34. HRMS (ESI) m/z calcd for C$_{14}$H$_{14}$N$_5$O$^+$ (M+H)$^+$ 268.11984, found 268.11887.

Compound 7h. $^1$H NMR (400 MHz, CDCl$_3$) δ 13.90 (s, 2H), 7.88 (s, 1H), 7.73-7.70 (m, 2H), 7.45-7.43 (m, 2H), 4.43 (d, J=3.4 Hz, 2H), 3.95-3.75 (m, 6H). $^{13}$C NMR (100 MHz, CDCl$_3$) δ 163.45, 141.31, 138.08, 136.96, 125.66, 122.06, 67.21, 66.83, 48.56, 44.04. HRMS (ESI) m/z calcd for C$_{15}$N$_{16}$N$_5$O$_2$$^+$ (M+H)$^+$ 298.13040, found 298.13037.

Compound 7i. $^1$H NMR (400 MHz, DMSO-d$_6$) δ 13.23 (s, 3H), 8.00 (s, 1H), 7.69 (s, 1H), 7.55 (s, 2H), 7.26-7.24 (m, 2H), 6.53-6.43 (m, 2H), 4.64 (d, J=4.9 Hz, 2H). $^{13}$C NMR (100 MHz, DMSO-d$_6$) δ 151.11, 141.92, 137.01, 122.16, 109.97, 106.81, 35.53. HRMS (ESI) m/z calcd for C$_{16}$H$_{14}$N$_5$O$_2$$^+$ (M+H)$^+$ 308.11475, found 308.11325.

Compound 7j. $^1$H NMR (400 MHz, DMSO-d$_6$) δ 13.34 (s, 1H), 13.05 (s, 1H), 12.82 (s, 1H), 8.00 (s, 1H), 7.60 (d, J=96.2 Hz, 3H), 7.23 (s, 3H), 7.05 (s, 1H), 4.85 (s, 2H). $^{13}$C NMR (100 MHz, DMSO-d$_6$) δ 158.61, 148.16, 142.17, 141.76, 138.08, 134.11, 130.61, 127.32, 126.62, 125.89, 123.53, 122.63, 118.57, 112.34, 38.16. HRMS (ESI) m/z calcd for C$_{16}$H$_{14}$N$_5$OS$^+$ (M+H)$^+$ 324.09191, found 324.09174.

Example 1: Bioactivity Assays

Materials and Methods

Reagents and Antibodies

Compounds were dissolved in a hydrous dimethylsulfoxide (DMSO, Life technologies) to obtain a 50 mM stock solution, which was then added to the culture medium at a concentration range of 6.25-100 μM. Cells were treated with compounds at indicated concentrations for 48 h, and 0.1% DMSO was used as the vehicle. Z-VAD-FMK was purchased from Selleckchem (Houston, Tex.); The reagents including 3-(4,5-dimethylthiazol-2-yl)-2,5-diphenyltetrazolium bromide (MTT), dimethyl sulfoxide (DMSO), penicillin, streptomycin, propidium iodide (PI) were purchased from Sigma-Aldrich (MO, USA); All the primary antibodies used in this study were from Cell Signaling Technology (MA, USA) and the secondary antibodies were from LI-COR Biosciences (NE, USA).

Cell Lines and Culture

Human triple negative breast cancer cell lines MDA-MB-231 and MDA-MB-468 were purchased from the American Type Culture Collection (ATCC, VA, USA). These cells were cultured in high-glucose DMEM (Gibco, USA) supplemented with 10% fetal bovine serum (FBS, Gibco) and 1% penicillin/streptomycin (Gibco) at 37° C. in a humidified incubator containing 5% CO$_2$.

Cell Viability Assay

The antiproliferative activity of compounds was measured with the MTT assay. Briefly, MDA-MB-231 and MDA-MB-468 cells were seeded into 96-well plates (3,000 cells/well) and incubated overnight at 37° C., then treated with 0, 6.25, 12.5, 25, 50 and 100 μmol/L test compounds for 24, 48 and 72 h. Next, 20 μL MTT solution (5 mg/mL) was added into each well and incubated for another 4 h, followed by media removal and solubilization in 200 μL DMSO. The absorbance value was determined at 570 nm using a microplate reader (Bio-Tek, VT, USA). Data were analyzed by GraphPad Prism 6. All experiments were performed in triplicates independently.

Colony Forming Assay

MAD-MB-231 and MDA-MB-468 cells were seeded in a six-well plate at 1000 cells/well and treated with various concentrations of compound 7a (0, 5, 10, 20 μmol/L) for 48 h. After discarding the supernatant, the cells were cultured with fresh medium for 15 days until formed the visible colonies. Finally, colonies were fixed with 4% paraformaldehyde (PFA) and stained with crystal violet for 30 min to enable enumeration of colonies.

Immunoblotting and Immunoprecipitation

MDA-MB-231 and MDA-MB-468 cells were treated with the compound 7a (0, 5, 10 and 20 μmol/L) for 48 h, total protein was extracted using RIPA buffer (Beyotime, Shanghai, China) supplemented with protease/phosphatase inhibitor cocktail (Roche, Mannheim, Germany) at 4° C. for 30 min. The protein concentration was quantified by the BCA protein assay kit (Beyotime). Protein samples (50 μg) were separated by SDS-PAGE with appropriate gel concentration and subsequent electrophoretically transferred onto PVDF membranes (Millipore Corporation, MA, USA). After blocking with 5% BSA for 2 h at ambient temperature, the membranes sections were incubated gently with the indicated primary antibodies overnight at 4° C. and washed with TBST for 5×5 minutes. Subsequently, the membranes were then incubated with corresponding IRDye 800CW goat anti-mouse IgG (H+L) or IRDye 680LT donkey anti-rabbit IgG (H+L) secondary antibody for 1 h. The objective protein signal was obtained using an odyssey two-color infrared fluorescence imaging system (Li-cor, NE, USA). For immunoprecipitation, harvested cells were lysed in ice-cold NP-40 buffer including 50 mM Tris-HCl (pH 7.4), 150 mM NaCl, 0.5% NP-40, 1 mM $Na_3VO_4$, 50 mM NaF and protease inhibitor cocktail (Roche). Lysate was centrifuged at 12,000×g for 20 min at 4° C. The supernatant was incubated with anti-HA at 4° C. overnight, followed by incubation with Protein-A/G beads overnight (Beyotime). The proteins were washed six times with ice-cold NP-40 buffer and eluted with SDS loading buffer containing mercaptoethanol by boiling for 10 min.

Flow Cytometry Analysis

Cells in a logarithmic growth phase were harvested and seeded into six-well plates with 30% cell density and cultured overnight in an incubator. Once adhered to the bottom of the plate, cells were treated with different doses of compound 7a for 48 h, and then employed in flow cytometry analysis. For cell cycle assay, the collected cells were washed with phosphate-buffered saline (PBS) and fixed with 70% cold ethanol in 4° C. for 24 h. After washing three times of PBS, the fixed cells were incubated in 200 μL PBS solution containing 1 μL propidium iodide (BD, CA, USA) and 1 μL RNase (Sigma Aldrich, USA) at 37° C. for 0.5 h. Finally, cells were analyzed using BD Accuri™ C6 flow cytometry (BD Biosciences, USA). For the cell apoptosis assay, after the cells were harvested and washed twice with PBS, the percentage of apoptotic cells were measured using an Annexin V-FITC/PI Apoptosis Assay Kit (BD Biosciences, USA). The BD Accuri™ C6 flow cytometry was used to analyze the apoptosis process. The FlowJo software was used to analyze the cell cycle arrest and apoptotic rate.

Mitochondrial Membrane Potential ($\Delta\Psi m$) Assay

The JC-1 Assay Kit (Beyotime) was used to monitor the alteration of mitochondrial membrane potential as the manufacturer's instructions. MDA-MB-231 and MDA-MB-468 cells were seeded in six-well plates with an appropriate density ($2\times10^5$/mL) and then treated with compound 7a at various concentrations (0, 5, 10, 20 μM) for 48 h. Then 100 μL of JC-1 staining solution was added into 1 mL of medium and incubated for 20 min at cell incubator. The BD Accuri™ C6 flow cytometry was used to analyze the samples. Each experiment was carried out in triplicate, and the results were expressed as the mean±SD.

Immunofluorescence

Cells were plated on glass coverslips in 24-well plates prior to treatment. After being exposed to different doses of compound 7a for 48 h, cells were washed with PBS for three times, fixed with 4% paraformaldehyde-PBS for 30 min, and then followed by permeabilization with 0.1% Triton X-100 for 10 min. Next, the samples were blocked with Quick-Block Blocking Buffer for Immunol Staining (Beyotime) for 30 min at 37° C., and incubated with anti-Ki67 (1:250), anti-LC3B antibody (1:250), anti-SQSTM1 antibody (1:250) or anti-γH2AX (1:250) overnight at 4° C. After washing with PBS three times, the stained cells were incubated with Alexa Fluor-conjugated secondary antibodies (1:2000) for 1 hour at room temperature. Moreover, 1 mg/mL DAPI dissolved in PBS were employed to label nuclei (30 min). Images were captured with a High Content analysis system (Perkinelmer, MA, USA).

Lentiviral Preparation and Viral Infection

Mcherry-EGFP-LC3B overexpression system was co-transfected with lenviral packaging vectors pSPAX2 and pMD2G into HEK293FT cells using Fugene Transfection Reagent (Promega, MW, USA). Virus particles were collected after 48 h infection, filtered through a 0.22 μm membrane, added into colorectal cancer cell HCT116, and then incubated for 12 h at 37° C. The medium was replaced and HCT116 cells were selected for puromycin tolerance (10 μg/mL) to obtain the stable cells expressing mcherry-EGFP-LC3B.

Animal Xenograft Model

For the in vivo assay, six-week-old female NOD/SCID mice weighing 16-20 g were used, which were maintained in the SPF (Specific Pathogen Free) laboratory animal environment and under a normal daily light/dark cycle. During the experiment, $1\times10^7$ MDA-MB-231 cells were suspended in 100 μL serum-free DMEM and injected subcutaneously into the left groin region of the mice. Tumor volume was measured regularly. On day 22 post-tumor implanted, the NOD/SCID mice were randomly divided into three groups (n=6) on the basis of their tumor volume to insure a similar starting tumor volume of all the groups. The appropriate dose of compound 7a (5 mg/kg, 15 mg/kg) dissolved in 100 μL solvent (10% ethanol, 40% PEG400 and 50% corn oil) was administered every 3 days by intraperitoneal injection when the xenograft tumor volume attained around 100 $mm^3$, while the control group received equal volume solvent every 3 days in a similar method. The tumor size was measured once every 3 days with a caliper, and tumor size was calculated using the standard formula $(L\times W^2)/2$, where L and W represents the length and width, respectively. The mice were sacrificed on Day 46 (Day 25 after treatment), and the xenograft tumors were obtained and weighed. Then the tumor tissues were collected and divided into two portions, one was fixed in 4% PFA and embedded by paraffin for Hematoxylin & eosin (HE) and immunohistochemical staining, anther was performed immunoblotting.

Immunohistochemical Staining

For immunohistochemistry, the embedded samples were sectioned and incubated with anti-Ki-67 overnight at 4° C. Then, the sections were incubated with HRP labeled secondary antibody and were observed under the Olympus BX73 microscope. Five fields were randomly selected to evaluate the positivity.

Statistical Analysis

All data were conducted more than three independent experiments. Statistical analysis was performed using GraphPad Prism 6. One-way ANOVA analysis, Student's t-test were applied to calculate the significance between different groups. The data were displayed as the mean±SD, and significance was set to $p<0.05$.

Results:

The Compound of Formula I Reduces TNBC Cell Viability and Proliferation

Figure 2:
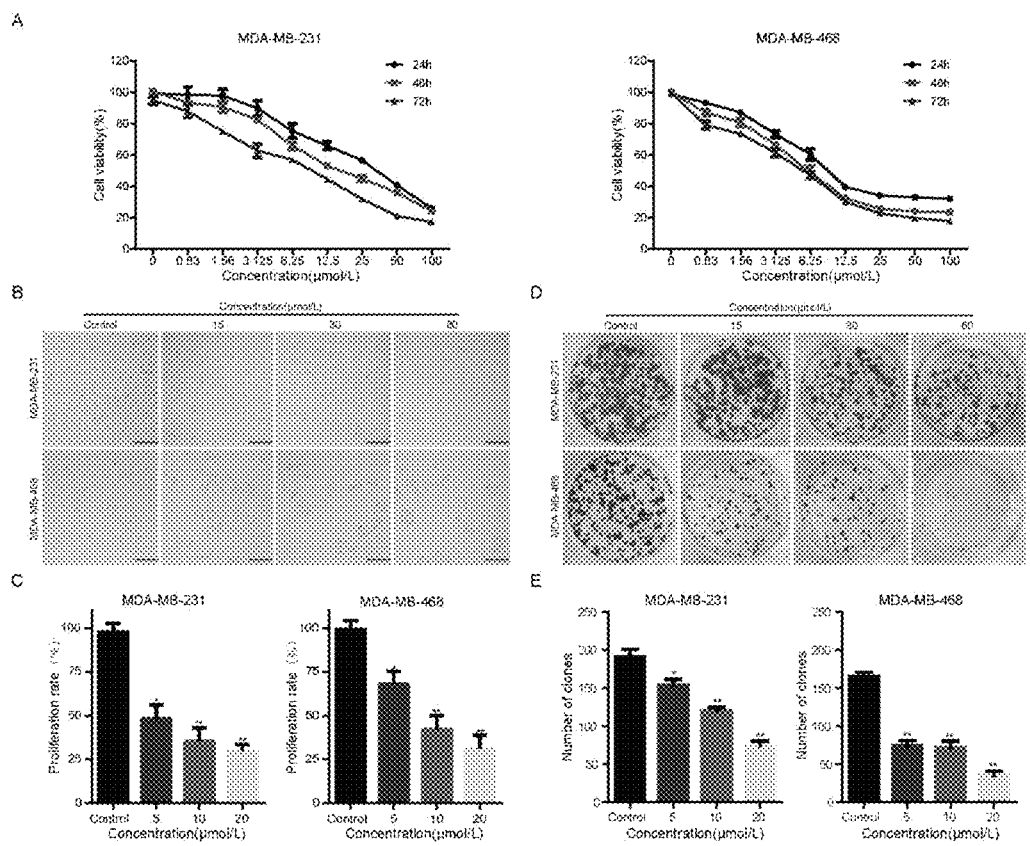
FIG. 2 shows the inhibition of TNBC cells proliferation and viability by the Compound 7a of the present application.

It was evaluated that whether the new synthesized benzimidazole derivatives could suppress proliferation and growth of TNBC cells. MTT assay showed that compound 7a can markedly inhibit the proliferation of TNBC cells (FIG. 2A). The $IC_{50}$ values in MDA-MB-231 and MDA-MB-468 cells were 8.3 μmol/L and 6.0 μmol/L, respectively (FIG. 2B), suggesting that compound 7a may be used as an inhibitor for TNBC treatment. Consistently, compound 7a efficiently inhibited TNBC cell viability in a time- and dose-dependent manner (FIG. 2A). Also, the cell counting assay with microscope showed that compound 7a significantly inhibited proliferation of TNBC cells (FIGS. 2B and 2C). Additionally, cells exposed to compound 7a exhibited a considerable survival inhibition, as evidenced by the smaller and decreased colony numbers (FIGS. 2D and 2E). Moreover, in comparison with controls, a notably reduced rate of Ki67-positive cells was observed in compound 7a-treated cells (FIG. 3A), indicating the growth inhibition role of compound 7a in TNBC cells.

The Compound of Formula I Blocks Cell Cycle Procession by Arresting TNBC Cells into S-Phase.

Figure 3:
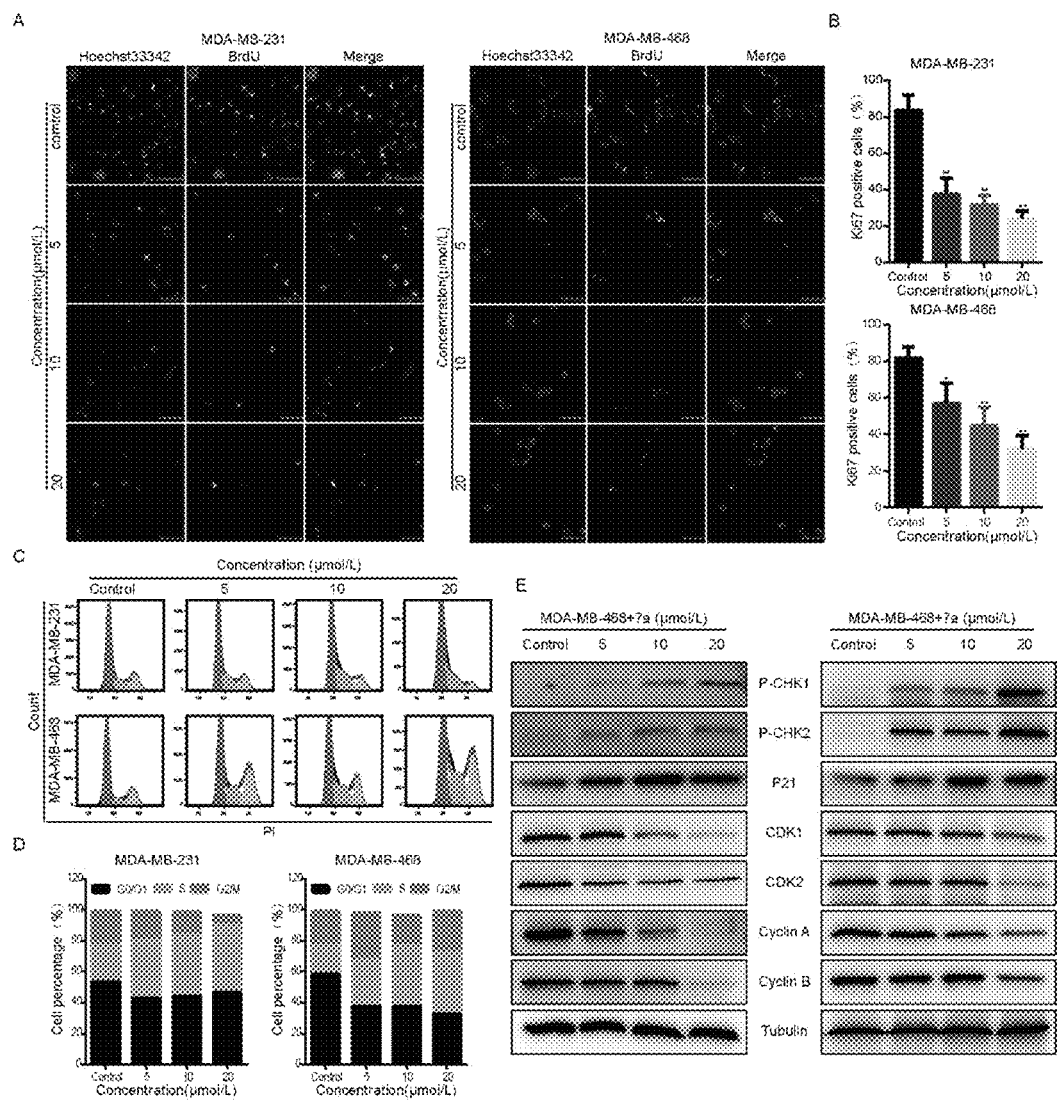
FIG. 3 shows that Compound 7a induces cell cycle arrest at S-phase to inhibit TNBC proliferation.

To deeply explore the mechanism underlying antiproliferative activity of the compound 7a in TNBC cells, cell cycle analysis was performed in TNBC cells treated with or without the inhibitor. As shown in FIG. 3C, the results obtained by flow cytometry indicated that compound 7a induced cell cycle arrest at S-phase in both MDA-MB-231 and MDA-MB-468 cells. The corresponding biometric data indicated that the percentage of S-phase cells was significantly increased after treatment with compound 7a (FIG. 3D). To further confirm the results, immunoblotting was performed to evaluate the levels of the S-phase related proteins. Consistently, cells exposure to compound 7a decreased the levels of Cyclin A, Cyclin B, CDK1 and CDK2, and however increased P21 and the phosphorylation levels of CHK1 (Serine 345) and CHK2 (Threonine 68) in a dose-dependent manner (FIG. 3E), implying that DNA damage is activated after treatment. Taken together, these results suggested that the compound 7a can inhibit cell proliferation by inducing S-phase cell cycle arrest because of the DNA damage induction.

Figure 4:
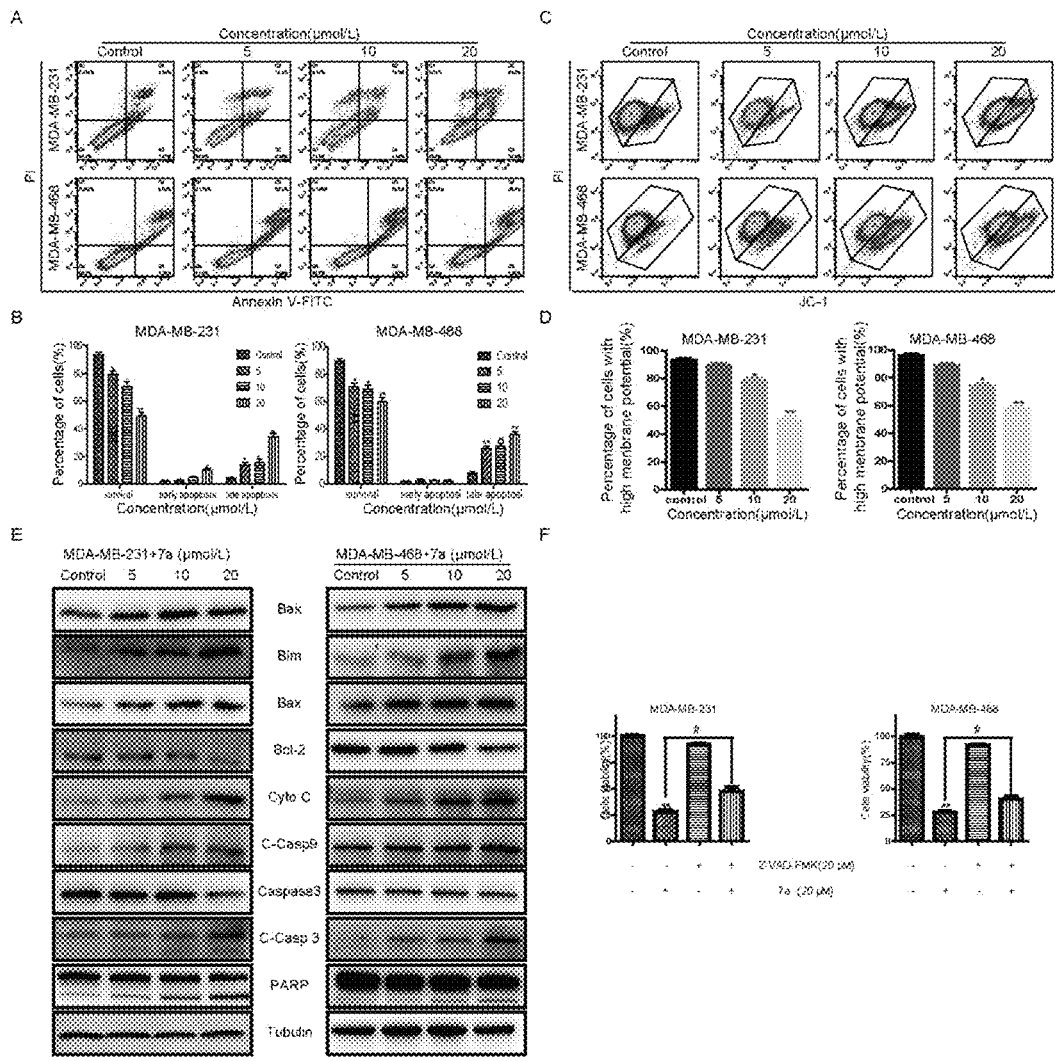
FIG. 4 shows that Compound 7a reduces the mitochondrial membrane potential and induces mitochondria-dependent intrinsic apoptosis in both MDA-MB-231 and MDA-MB-468 cells.

The Compound of Formula I Induces Mitochondria-Dependent Apoptosis in TNBC Cells To gain more insights into the mode of compound 7a-induced proliferation suppression, an Annexin V-FITC/PI assay was performed via flow cytometry after MDA-MB-231 and MDA-MB-468 cells were exposed to the compound 7a for 48 h. As shown in FIGS. 4A and 4B, the results of flow cytometry analysis showed that compound 7a could dramatically induce cell apoptosis in TNBC cells and considerably increase the proportion of late-phase apoptosis (from 3.64% to 34.2% for MDA-MB-231 cells, $p<0.01$; from 5.02% to 36.4% for MDA-MB-468 cells, $p<0.01$) in a dose-dependent manner. Furthermore, to evaluate whether the mitochondrial membrane potential and integrity were damaged by compound 7a treatment, TNBC cells exposed to compound 7a were stained with JC-1 to measure the $\Delta\Psi m$. Compared with the control group, compound 7a treatment induced a dose-dependent decrease in $\Delta\Psi m$ (FIGS. 4C and 4D). The results showed that the mitochondrial membrane potential of nearly 50% of MDA-MB-231 and MDA-MB-468 cells was reduced after exposure to 20 μM/L of compound 7a for 48 h (FIG. 4D). This implies that the apoptosis induced by compound 7a might be associated with the decrease in $\Delta\Psi m$ of mitochondrial membrane. Also, immunoblotting was employed to confirm the apoptotic effects of compound 7a. Consistently, TNBC cells treated with compound 7a resulted in a decrease of anti-apoptotic protein Bcl-2, while the expressions of pro-apoptotic proteins such as Bak, Bim and Bax were elevated in a dose-dependent manner. Moreover, after treatment with compound 7a, it was observed that cytochrome c, cleaved caspase-3, cleaved caspase-9 and cleaved PAPR were increased in a dose-dependent manner in both MDA-MB-231 and MDA-MB-468 cells (FIG. 4E). Interestingly, a pan-caspase inhibitor, Z-VAD-FMK, could partially rescue cell apoptosis induced by compound 7a when treated with both of them (FIG. 4F). In summary, these data indicate that apoptotic effect of compound 7a depends on the activation of apoptosis-related proteins through a mitochondria-dependent apoptotic pathway in TNBC cells.

Figure 5:
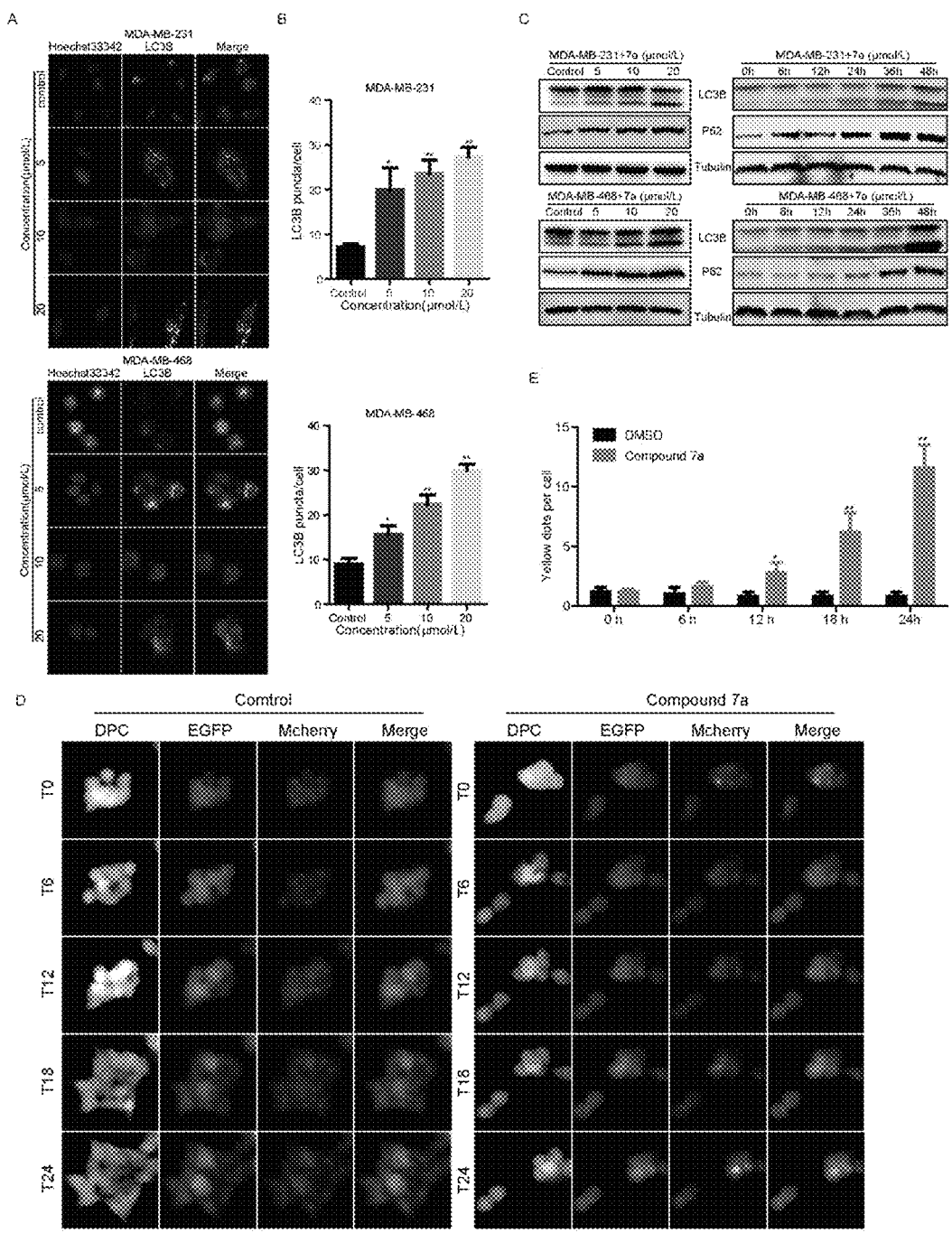
FIG. 5 shows that Compound 7a initiates autophagy while suppresses autophagic flux in TNBC cells.

The Compound of Formula I Initiates Autophagy while Blocks the Fusion of Autophagosomes and Lysosomes in TNBC Cells Because autophagy plays a vital role in sustaining cancer cell survival under stressful conditions and might mediate tolerance to some treatments such as chemotherapy, radiation and target drugs used in patients, it was explored that whether the autophagy was influenced in response to compound 7a. Autophagy activation was detected through monitoring the conversion from the cytosolic form, LC3B-I, to the autophagosome associated form, LC3B-II, a specific and conserved marker of autophagy. Of note, conversion to LC3B-II was significantly induced in both of the TNBC cells, which were exposed to compound 7a, in a dose- and time-dependent manner, indicating that autophagy was activated after treatment (FIGS. 5A, 5B and 5C). To further determine the effect of compound 7a on the progression of autophagic flux, it was tested that whether p62, which is a marker of blockage of fusion between autophagosome and lysosome, was accumulated after treatment. The result showed that compound 7a treatment resulted in a p62 accumulation in TNBC cells (FIGS. 5C, 6E, 6F and 6G). In order to confirm whether compound 7a could induce the blockage of autophagic flux, double tagged mCherry-GFP-LC3B reporter, which is pH sensitive, was transfected into colorectal cancer cell line HCT116 to examine the fusion efficiency of autophagosome and lysosome. The yellow fluorescent represented the number of non-acidic autophagosomes, while the red fluorescent labeled autolysosomes. As shown in FIGS. 5D and 5E, a significant increase in the number of yellow fluorescent vesicles of compound 7a-treated HCT116 cells was observed as compared with control after 12 h treatment, implying that accumulation of autophagosomes was caused by a defect of fusion between autophagosome and lysosome. In conclusion, these data indicated that compound 7a initiated the autophagy while led to the blockage of autophagic flux and p62 accumulation in cancer cells.

Figure 6:
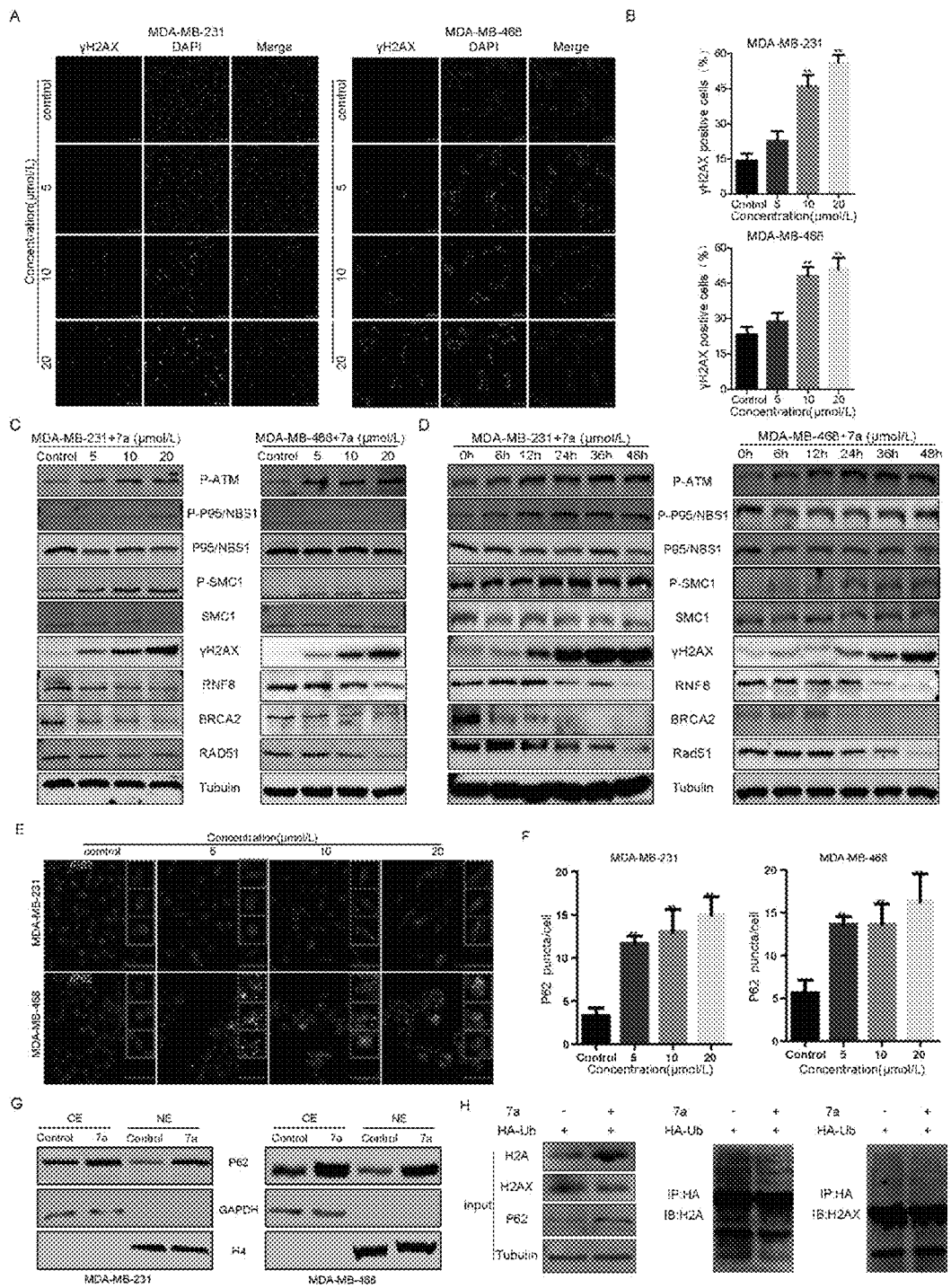
FIG. 6 shows that Compound 7a activates DDR-signaling cascade whereas impairs DNA repair because of deficiency of H2A ubiquitination in a p62-dependent manner.

Autophagic Flux Inhibition Induced by the Compound of Formula I Provokes DDR Whereas Inhibits DNA Repair Herein, it was investigated that whether compound 7a could affect the DNA damage and repair processes in response to the autophagic flux inhibition. It is reported that γH2AX, the phosphorylated histone H2AX, is the marker of DNA double strand breaks. Hence, immunofluorescence assay was performed to detect whether compound 7a could lead to DNA damage in both MDA-MB-231 and MDA-MB-468 cells. As shown in FIGS. 6A and 6B, it was found that TNBC cells treated with compound 7a resulted in an accumulation of γH2AX foci in nuclei, but not found in the control group. Consistently, immunoblotting also showed that γH2AX was significantly increased in the presence of compound 7a in a dose-dependent manner (FIGS. 6C and 6D), indicating that DNA double strand breaks could appear in TNBC cells due to compound 7a treatment. Furthermore, to determine whether compound 7a treatment induced the activation of DNA damage response, the phosphorylation/activation of the DNA sensor markers, including ATM, NBS1 and SMC1 were also analyzed. Immunoblotting analysis showed that the phosphorylation of ATM, NBS1 and SMC1 were activated in response to compound 7a, implying that DDR was induced upon the treatment (FIGS. 6C and 6D). Next, to evaluate if compound 7a impaired the DNA repair (DR) in TNBC cells, the expression levels of DR-related proteins after compound 7a treatment, including BRCA2 and RAD51, were tested. As shown in FIGS. 6C and 6D, it was found that compound 7a dramatically decreased levels of both proteins in a dose-dependent manner, suggesting that compound 7a induced DR deficiency.

Suppression of Autophagic Flux by the Compound of Formula I Impairs DR Through Down-Regulating Chromatin Ubiquitination in a p62-Dependent Manner Previous reports indicated that impaired nuclear localized p62 elimination was the cause of diminished DNA repair kinetics. Nuclear p62 accumulation due to loss of autophagy promotes proteasome degradation of RAD51 within the nucleus, leading to a decreased level of RAD51. Therefore, to confirm whether the detailed molecular mechanism of compound 7a regulating the DNA repair process depends on nuclear localized p62, the expression levels of p62 in nuclear and cytoplasm was evaluated. As shown in FIGS. 6E and 6F, the green signal representing p62 accumulated in the nuclei of both MDA-MB-231 and MDA-MB-468 cells in a dose-dependent manner. Consistently, as detected by immunoblotting, a drastic p62 increase in the nucleus and cytoplasm in a dose-dependent manner after treatment with compound 7a was observed (FIG. 6G). These results indicated that compound 7a not only induced accumulation of cytoplasm p62 but also nucleus p62. Then, RAD51 level was detected to explore the effect of accumulated p62 in the nucleus, and the result showed that RAD51 was decreased in a time- and dose-dependent manner after being exposed to compound 7a (FIGS. 6C and 6D). Since accumulation of p62 in nuclei has a negative effect on the chromatin ubiquitination and the subsequent recruitment of DNA repair-related proteins to the DNA damage site, next immunoblotting was performed to analyze the level of RNF8, which is an E3 ubiquitin ligase for the recruitment of RNf168 to the DNA damage foci. Interestingly, it was found that the expression of BRCA2, RAD51 and RNF8 were significantly reduced in TNBC cells after exposure to compound 7a (FIGS. 6C and 6D). It has been reported that H2A/H2AX ubiquitination catalyzed by RNF8 and RNF168 is vital for the recruitment of downstream regulators of the DSB response pathway to complete the DDR process. Therefore, it would be interesting to investigate whether H2A/H2AX ubiquitination is influenced by the reduction of RNF8 E3 ligases. As expected, DNA-damage-induced formation of H2A poly-ubiquitin chains was significantly reduced, but the ubiquitination of H2AX was not (FIG. 6H). These observations indicated that compound 7a impairs DR through leading to a deficiency of DNA repair protein recruitment to the DSB sites. In summary, these data indicated that increased p62 induced by compound 7a suppressed RNF8-mediated H2A poly-ubiquitination, and then impaired the recruitment of downstream factors, such as BRCA2 and Rad51, to DNA damage sites to perform the process of DNA repair, suggesting that compound 7a is an activator of DNA damage and inhibitor of DNA repair for the cell cycle arrest and apoptosis activation.

The Compound of Formula I Exhibits Strong Anti-Tumor Activity In Vivo

Figure 7:
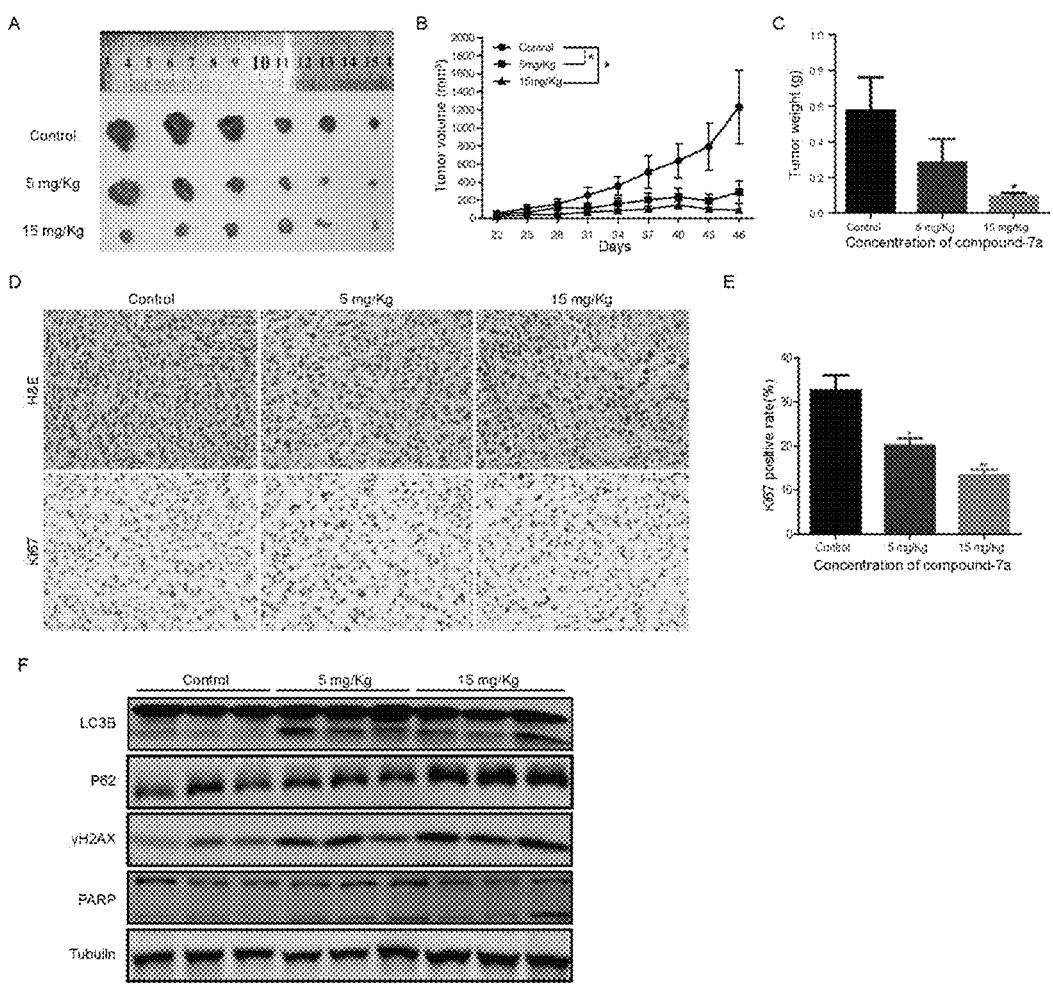
FIG. 7 shows that Compound 7a suppresses tumor growth in TNBC xenograft. MDA-MB-231 was injected into flanks of 6-week-old SCID/NOD mice.

Inhibition of DNA damage and fast repair after formation of DSBs are two critical hallmarks of cancer cell survival and cancer drug resistance, and therefore targeting both events is a truly approach to cancer treatment. Since it was acquired that compound 7a effectively initiates DNA damage and inhibits DNA repair, the effect of compound 7a on suppression of tumor formation in vivo was further evaluated. As presented in FIG. 7A, tumors harvested from mice treated with compound 7a were dramatically smaller than tumors from vehicle-treated control mice. Importantly, compound 7a treatment at concentrations of 5 and 15 mg/Kg considerably suppressed human TNBC tumor growth after 24 days in a dose dependent manner in comparison with vehicle-treated control mice in xenograft animal model (FIGS. 7B and 7C). Consistently, hematoxylin and eosin (H&E) staining and immunohistochemistry results showed a significant decrease in cell count and Ki67, which is a critical marker for cell proliferation (FIGS. 7D and 7E). Next, immunoblotting analysis using tumor tissues was performed to confirm whether the in vitro results were reappeared in nude mice model. Of note, compound 7a resulted in a concentration-dependent upregulation of LC3B-II, p62, γH2AX and PARP. These results collectively offer convincing pharmacological evidence that compound 7a can be used as an anti-tumor inhibitor for the treatment of human TNBC.

In the present application, a series of benzimidazole-derivatives have been synthetized and exhibited some extent anti-proliferation activity against TNBC cells, for example, compound 7a exhibited potent activity to both MDA-MB-231 and MDA-MB-468 cell lines.

Cell cycle arrest and apoptosis induction are two major pathways to inhibit tumor cell progression. Herein, it was demonstrated that compound 7a significantly suppressed TNBC cells proliferation and colony formation ability in a dose- and time-dependent manner, confirming the inhibitory effect of compound 7a on TNBC. Furthermore, it was found that exposure to compound 7a induced remarkable cell cycle arrest at S-phase in MDA-MB-231 and MDA-MB-468 cells through measurement of flow cytometric and detection of corresponding cycle proteins. Numerous anti-cancer agents also execute their inhibitory effect by promoting apoptosis, which is mediated through two major pathways: the mitochondria-mediated intrinsic pathway and the death-receptorinduced extrinsic pathway. The anti-apoptotic and pro-apoptotic members of the Bcl-2 protein family play an imperative role in the mitochondria-mediated apoptosis pathway. The activation of intrinsic pathway will result in dramatic cleavage of downstream caspases such as caspase-3, caspase-9 and PARP, suggesting the induction of mitochondrial-mediated apoptosis. The data presented herein showed that compound 7a could induce the increase of Bak, Bim, Bax and release of cytochrome c, while results in the decrease of Bcl-2. Then, the cleavages of caspase 3, caspase 9 and PARP were induced after treatment with compound 7a, indicating that apoptotic effect is related to the mitochondrial pathway. Thus, the inhibitory role of compound 7a in TNBC cells may partly depend on cell cycle arrest and mitochondria-mediated apoptosis.

To further illuminate the molecular mechanism underlying the activation of cell cycle arrest and apoptosis, the biological activities of compound 7a in pathways that play important effects on tumor suppression were examined. At present, some existing chemotherapeutic agents inhibit human cancer cells by inducing genomic DNA damage which deeply initiates cell cycle arrest and cell death programs. DNA damage triggers activation of DDR factors, including ATM and ATR. The results herein indicated that TNBC cells exposed to compound 7a induced phosphorylation of ATM kinase and their downstream effectors H2AX, BRCA2, P95 and SMC1, suggesting that cells suffered compound 7a mediated DNA damage and activated the DDR pathway. Subsequently, downstream factors involved in cell cycle progression, apoptosis and cell survival were affected by these upstream signals. Furthermore, accumulation of γH2AX in DNA damage sites implied that the DNA strand breaks were induced after treatment with compound 7a, which was the most catastrophic form of DNA damage. Once DSBs formed, cells will use either one or both of the two major pathways, HR and NHEJ, to repair. HR is vital to cell survival but its activity is limited to cells during late S- or G2-phases of the cell cycle because the replicated DNA strand is served as a template. Herein, it was found that RAD51, a homologous recombination repair protein, was remarkably reduced in dose- and time-dependent manner after treatment with compound 7a, demonstrating that DNA damage repair was inhibited by suppressing abundance of HR related proteins. Additionally, compound 7a triggered the S-phase arrest in TNBC cells, and therefore the substantial loss of HR may cause great effect on cell fate and compound 7a-induced cell apoptosis.

Several reports have indicated that autophagy acts as a DNA repair-promoting cellular pathway through affecting chromatin ubiquitination. During this process, p62, an ubiquitin and LC3 binding protein, has been suggested as a link between histone ubiquitination and DNA damage repair. RNF8-dependent conjugation of ubiquitin on histone H1 initiates and responses to the DSB-induced ubiquitination cascade. Then, RNF8 recruits another E3 ligase, RNF168, to catalyze the ubiquitin-K63 linked chains on K13-15 of H2A and H2AX. This histone ubiquitination regulation is a prerequisite for the further recruitment of downstream effectors of the DSB response pathway, such as RAD51, BRCA1, RAP80 and 53BP1 complex. However, nuclear accumulated p62 due to loss of autophagy directly binds to and reduces nuclear RNF168, and then DNA repair proteins cannot be recruited to the sites of DSBs, which leads to impaired DNA repair. Consistently, the data herein indicated that p62 was upregulated because the fusion of autophagosome and lysosome was blocked after treatment with compound 7a. Also, the level of RNF8 along with H2A ubiquitination were significantly reduced upon compound 7a treatment. Meanwhile, the DR effectors such as RAD51 and BRCA2 were also decreased because of the p62 accumulation induced H2A ubiquitination loss. Accordingly, compound 7a may suppress DNA repair through inhibition of histone ubiquitination due to autophagy deficiency. Thus, compound 7a may play a role as an inhibitor of RNF8-RNF168-H2A pathway to suppress H2A ubiquitination. Then, the recruitment of downstream effectors to DSB sites is blocked because of H2A ubiquitination deficiency induced by p62 accumulation upon compound 7a treatment. Additionally, upon induction of DNA damage, p62 shuttles into nucleus and promotes the proteasomal degradation of RAD51 within the nucleus, leading to decreased levels of nuclear RAD51 and delayed DNA repair. RAD51 is downstream effector of p62 and mediates the role of p62 in DR. Interestingly, in the present application, it was observed that the abundance of RAD51 was remarkably reduced while p62 was accumulated resulting from autophagy deficiency after treatment with compound 7a. Accordingly, nuclear p62 accumulation from compound 7a treatment inducing autophagic flux deficiency may lead to proteasomal degradation of RAD51, which results in the inhibition of DR mediated by this protein. These data are consistent with previous reports and also confirm the effect of autophagy and p62 on DR. Therefore, compound 7a can be used as a novel inhibitor which affects autophagy and E3 ubiquitin ligase for histone ubiquitination, and then suppress the recruitment of effectors related to HR.

In conclusion, the present application provides a novel inhibitor which induces DNA damage and inhibits DNA repair in TNBC cells by triggering the accumulation of p62 due to suppression of the autophagic flux. Interestingly, nuclear p62 accumulation induced by compound 7a results in the inhibition of RNF8-mediated chromatin ubiquitination and the degradation of HR-related proteins in regulating the DDR process. The findings herein indicate that compound 7a is a specific DNA damage response modulator and could be developed as an agent for further cancer therapeutics.

The preceding description of the disclosed embodiments is provided to enable any person skilled in the art to make or use the present application. Various modifications to these embodiments will be readily apparent to those skilled in the art, and the generic principles defined herein may be applied to other embodiments without departing from the scope of the invention. Thus, the present application is not intended to be limited to the embodiments shown herein but is to be accorded the widest scope consistent with the principles and novel features disclosed herein. Further, any reference to claim elements in the singular, for example, using the articles "a," "an," or "the," is not to be construed as limiting the element to the singular.

What is claimed is:

1. A compound of Formula I or a pharmaceutically acceptable salt thereof,

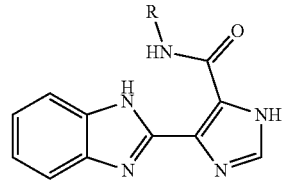

Formula I wherein, R is selected from the group consisting of optionally substituted cycloalkyl, optionally substituted heterocycloalkyl, optionally substituted alkenyl, and optionally substituted alkynyl.

2. The compound according to claim 1, wherein, R is selected from the group consisting of cycloalkyl, heterocycloalkyl, alkenyl, and alkynyl, each of which is independently optionally substituted with one or more substituents independently selected from the group consisting of halo, alkyl, —N(R¹)₂, —NR¹R², —S(=O)R¹, —S(=O)₂R¹, —C(=O)R¹, —N(R¹)C(=O)R², —N(R¹)C(=O)R¹, and —(CH₂)ₜP(=O)(OR¹)₂ wherein t is 0, 1, or 2,
wherein each R¹ and each R² are independently alkyl, alkenyl, alkynyl, and heterocyclyl, each of which is optionally substituted by halo, —CN, —NO₂, —NH₂, —NHCH₃, —NHCH₂CH₃, oxo, —OH, —OCH₃ or 3- to 6-membered heterocyclyl.

3. The compound according to claim 1, wherein R is selected from the group consisting of optionally substituted C₃₋₂₀ cycloalkyl, optionally substituted C₂₋₂₀ heterocycloalkyl, optionally substituted C₂₋₂₀ alkenyl, and optionally substituted C₂₋₂₀ alkynyl, or R is selected from the group consisting of optionally substituted C₃₋₁₅ cycloalkyl, optionally substituted 3- to 15-membered heterocycloalkyl, optionally substituted C₂₋₁₅ alkenyl, and optionally substituted C₂₋₁₅ alkynyl, or R is selected from the group consisting of optionally substituted C₃₋₁₂ cycloalkyl, optionally substituted 3- to 12-membered heterocycloalkyl, optionally substituted C₂₋₁₀ alkenyl, and optionally substituted C₂₋₁₀ alkynyl.

4. The compound according to claim 1, wherein R is 3- to 8-membered cycloalkyl or 5- to 6-membered heterocycloalkyl.

5. The compound according to claim 1, wherein the compound of Formula I or a pharmaceutically acceptable salt thereof is selected from:

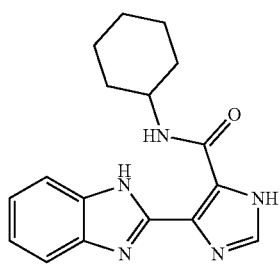

7a

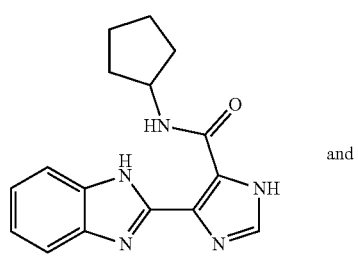

7f and

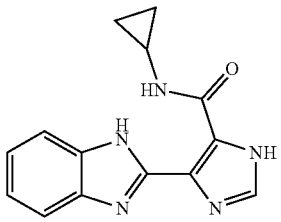

7g or a pharmaceutically acceptable salt thereof.

6. A pharmaceutical composition comprising a compound of Formula I or a pharmaceutically acceptable salt thereof, and one or more pharmaceutically acceptable carriers or excipients,

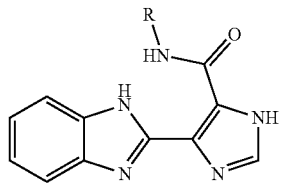

Formula I wherein, R is selected from the group consisting of optionally substituted cycloalkyl, optionally substituted heterocycloalkyl, optionally substituted alkenyl, and optionally substituted alkynyl.

7. The pharmaceutical composition according to claim 6, wherein, R is selected from the group consisting of cycloalkyl, heterocycloalkyl, alkenyl, and alkynyl, each of which is independently optionally substituted with one or more substituents independently selected from the group consisting of halo, alkyl, —N(R¹)₂, —NR'R², —S(=O)R¹, —S(=O)₂R¹, —C(=O)R¹, —N(R¹)C(=O)R², —N(R')C(=O)R¹, and —(CH₂)ₜP(=O)(OR¹)₂ wherein t is 0, 1, or 2,
wherein each R¹ and each R² are independently alkyl, alkenyl, alkynyl, and heterocyclyl, each of which is optionally substituted by halo, —CN, —NO₂, —NH₂, —NHCH₃, —NHCH₂CH₃, oxo, —OH, —OCH₃ or 3- to 6-membered heterocyclyl.

8. The pharmaceutical composition according to claim 6, wherein R is selected from the group consisting of optionally substituted C₃₋₂₀ cycloalkyl, optionally substituted C₂₋₂₀ heterocycloalkyl, optionally substituted C₂₋₂₀ alkenyl, and optionally substituted C₂₋₂₀ alkynyl, or R is selected from the group consisting of optionally substituted C₃₋₁₅ cycloalkyl, optionally substituted 3- to 15-membered heterocycloalkyl, optionally substituted C₂₋₁₅ alkenyl, and optionally substituted C₂₋₁₅ alkynyl, or R is selected from the group consisting of optionally substituted C₃₋₁₂ cycloalkyl, optionally substituted 3- to 12-membered heterocycloalkyl, optionally substituted C₂₋₁₀ alkenyl, and optionally substituted C₂₋₁₀ alkynyl.

9. The pharmaceutical composition according to claim 6, wherein R is 3- to 8-membered cycloalkyl or 5- to 6-membered heterocycloalkyl.

10. The pharmaceutical composition according to claim 6, wherein the compound of Formula I or a pharmaceutically acceptable salt thereof is selected from:

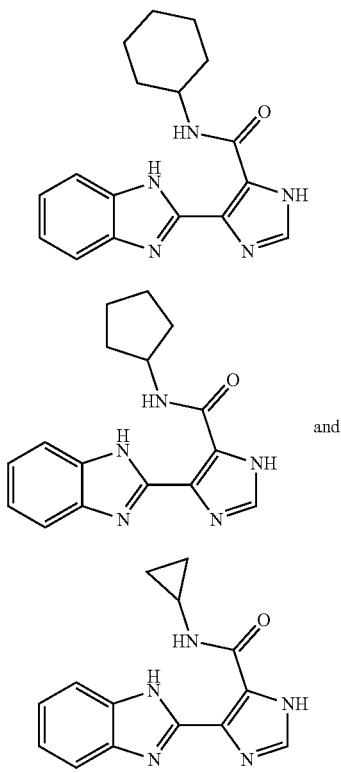

or a pharmaceutically acceptable salt thereof.

11. A method for treating a disease benefiting from the inhibition of autophagic flux and/or chromatin ubiquitination, comprising administering to a subject in need thereof a therapeutically effective amount of a compound of Formula I or a pharmaceutically acceptable salt thereof,

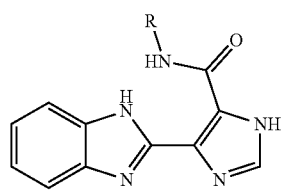

Formula I wherein, R is selected from the group consisting of optionally substituted cycloalkyl, optionally substituted heterocycloalkyl, optionally substituted alkenyl, optionally substituted alkynyl, and optionally substituted heteroaryl.

12. The method according to claim 11, wherein R is selected from the group consisting of cycloalkyl, heterocycloalkyl, alkenyl, alkynyl, and heteroaryl, each of which is independently optionally substituted with one or more substituents independently selected from the group consisting of halo, alkyl, haloalkyl, cyano, aryl, alkoxy, alkoxyaryl, heteroaryl, ester group, $-N(R^1)_2$, $-NR^1R^2$, $-S(=O)R^1$, $-S(=O)_2R^1$, $-C(=O)R^1$, $-N(R')C(=O)R^2$, $-N(R^1)C(=O)R^1$, and $-(CH_2)_tP(=O)(OR^1)_2$ wherein t is 0, 1, or 2, wherein each $R^1$ and each $R^2$ are independently alkyl, alkenyl, alkynyl, and heterocyclyl, each of which is optionally substituted by halo, $-CN$, $-NO_2$, $-NH_2$, $-NHCH_3$, $-NHCH_2CH_3$, oxo, $-OH$, $-OCH_3$ or 3- to 6-membered heterocyclyl.

13. The method according to claim 11, wherein R is selected from the group consisting of optionally substituted $C_{3-20}$ cycloalkyl and optionally substituted 3- to 20-membered heterocycloalkyl, optionally substituted $C_{2-20}$ alkenyl, optionally substituted $C_{2-20}$ alkynyl, and optionally substituted 5- to 20-membered heteroaryl, or R is selected from the group consisting of optionally substituted $C_{3-15}$ cycloalkyl and optionally substituted 3- to 15-membered heterocycloalkyl, optionally substituted $C_{2-15}$ alkenyl, optionally substituted $C_{2-15}$ alkynyl, and optionally substituted 5- to 15-membered heteroaryl, or R is selected from the group consisting of optionally substituted $C_{3-12}$ cycloalkyl and optionally substituted 3- to 12-membered heterocycloalkyl, optionally substituted $C_{2-10}$ alkenyl, optionally substituted $C_{2-10}$ alkynyl, and optionally substituted 5- to 12-membered heteroaryl.

14. The method according to claim 11, wherein R is 3- to 8-membered cycloalkyl or 5- to 6-membered heterocycloalkyl.

15. The method according to claim 11, wherein the compound of Formula I or a pharmaceutically acceptable salt thereof is selected from:

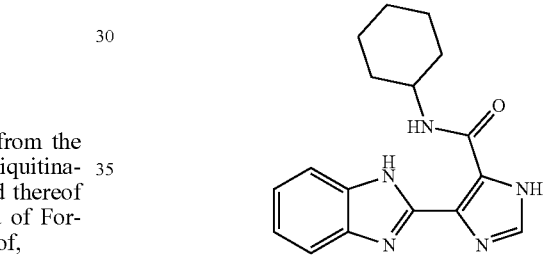

or a pharmaceutically acceptable salt thereof.

16. The method according to claim 11, wherein the disease is breast cancer.

17. The method according to claim 16, wherein the breast cancer is triple negative breast cancer.

* * * * *

UNITED STATES PATENT AND TRADEMARK OFFICE
CERTIFICATE OF CORRECTION

PATENT NO. : 11,512,073 B2
APPLICATION NO. : 17/346161
DATED : November 29, 2022
INVENTOR(S) : Chen et al.

It is certified that error appears in the above-identified patent and that said Letters Patent is hereby corrected as shown below:

In the Claims

Column 30, Claim 7, Lines 39-42:
Delete "-NR'R$^2$, -S(=O)R$^1$, -S(=O)$_2$R$^1$, -C(=O)R$^1$, -N(R$^1$)C(=O)R$^2$, -N(R')C(=O)R$^1$,"
And replace with -- -NR$^1$R$^2$, -S(=O)R$^1$, -S(=O)$_2$R$^1$, -C(=O)R$^1$, -N(R$^1$)C(=O)R$^2$, -N(R$^1$)C(=O)R$^1$, --

Column 31, Claim 12, Line 62:
Delete "-N(R')C(=O)R$^2$,"
And replace with -- -N(R$^1$)C(=O)R$^2$, --

Signed and Sealed this
Twenty-first Day of February, 2023

Katherine Kelly Vidal
*Director of the United States Patent and Trademark Office*